United States Patent
Wang et al.

(10) Patent No.: US 7,700,908 B2
(45) Date of Patent: Apr. 20, 2010

(54) TWO DIMENSIONAL OPTICAL SCANNING IMAGE SYSTEM

(75) Inventors: Wei-Chih Wang, Sammamish, WA (US); Per G. Reinhall, Seattle, WA (US)

(73) Assignee: University of Washington, Seattle, WA (US)

( * ) Notice: Subject to any disclaimer, the term of this patent is extended or adjusted under 35 U.S.C. 154(b) by 0 days.

(21) Appl. No.: 11/760,622

(22) Filed: Jun. 8, 2007

(65) Prior Publication Data
US 2008/0304123 A1 Dec. 11, 2008

(51) Int. Cl.
*H01J 3/14* (2006.01)

(52) U.S. Cl. ...................... 250/234; 250/216
(58) Field of Classification Search ................. 250/234, 250/216; 385/8; 359/245
See application file for complete search history.

(56) References Cited

U.S. PATENT DOCUMENTS

| | | | |
|---|---|---|---|
| 3,976,360 A * | 8/1976 | Schroder | 359/303 |
| 4,902,088 A | 2/1990 | Jain et al. | |
| 5,276,745 A | 1/1994 | Revelli, Jr. | |
| 5,761,350 A | 6/1998 | Koh | |
| 5,920,662 A * | 7/1999 | Hinkov | 385/14 |
| 6,381,490 B1 | 4/2002 | Ostrovsky | |
| 6,385,355 B1 | 5/2002 | Nashimoto et al. | |
| 2003/0040134 A1 | 2/2003 | Deliwala | |
| 2005/0238277 A1 * | 10/2005 | Wang et al. | 385/8 |

FOREIGN PATENT DOCUMENTS

FR 2 764 398 12/1998

OTHER PUBLICATIONS

PCT/US2005/006829, PCT Search Report and Written Opinion, dated Jun. 3, 2005.
Revelli, J., "High-resolution electrooptic surface prism waveguide deflector: an analysis," Applied Optics, Feb. 1, 1980, pp. 389-397, vol. 19, No. 3, Optical Society of America, New York.

* cited by examiner

*Primary Examiner*—Thanh X Luu
(74) *Attorney, Agent, or Firm*—Blakely Sokoloff Taylor & Zafman LLP

(57) ABSTRACT

An ultra high speed miniature two dimensional electro-optic image acquisition system uses prisms of varying geometries to control the amount of horizontal deflection and a Bragg grating to control the amount of vertical deflection. A collimating lens array and a Gaussian profile Bragg grating help confine the beam diameter of the deflected light beam. A separate prism further bends light into the vertical direction. A spherical lens focuses light onto a photodetector array for display.

17 Claims, 12 Drawing Sheets

TWO DIMENSIONAL OPTICAL SCANNING IMAGE SYSTEM

STATEMENT REGARDING FEDERALLY-SPONSERED RESEARCH

This invention was made with government support under grand number 5R21 EB004564 awarded by the National Institutes of Health. The government has certain rights in the invention.

BACKGROUND

1. Field

Embodiments of the present invention relate to optics and, in particular, to image scanning.

2. Discussion of Related Art

Flexible endoscopes are commonly used in medical applications to look inside the human body to check the status of such organs as lungs, intestines, and colon, for example. Presently available flexible scope designs use either a bundle of optical fibers, typically in a tube, and/or one or more cameras having an array of detectors to capture an image.

Many commercially available endoscopes suffer from a fundamental tradeoff between high image quality and small size, however. For example, the diameter of currently available flexible endoscopes cannot be reduced to smaller than the image size. The diameter also is limited by the individual pixel size of a camera or by the diameter of optical fibers used to acquire the image. Currently, the smallest pixel element is determined by the size of the end of an optical fiber, which has a minimum core diameter of about four micrometers (4 μm). To propagate light through an optical fiber, a surrounding cladding layer is required. The cladding requirement increases the minimum pixel size to more than 5 μm in diameter. If a standard video graphics adapter (SVGA) image is desired, (e.g., with a resolution of 640×480 pixels), then a minimum diameter required for just the imaging optical fiber is more than three millimeters (3 mm). Larger diameters adversely affect the fineness of detail that can be distinguished in an image or resolution. Larger diameters also adversely affect the area that is visible through the endoscope or field of view (FOV). Therefore, to achieve endoscopes with less than 3 mm overall diameter using current technologies, resolution and/or field of view must be sacrificed by having fewer pixel elements.

Currently available endoscopes also suffer from poor control mechanisms. Some optical systems use an optical fiber and a charge coupled device (CCD) camera at a tip of the flexible fiber to illuminate a region of interest and acquire an image. The optical fiber and camera are manually controlled by a practitioner positioning the tip of the flexible fiber. Other optical systems use a resonant fiber that is actuated into resonance with one or more nodes to produce a desired illumination spot. Although these systems actuate the fiber, such systems cannot precisely control the position of the fiber tip without adding material to the fiber scan system and increasing the diameter and/or tip length.

Other optical systems deflect or move mirrors to position the light beam rather than move the waveguide. However, the mirrors must be larger than the light beam diameter to avoid clipping the beam or adding diffraction. Thus, the mirrors must be larger than the waveguide, thereby increasing the overall size of the instrument.

Some microscopes actuate a cantilever waveguide for near-field imaging. However, near-field systems have a very limited field of view (e.g., typically less than 500 nanometers), and a light-emitting tip must be positioned within nanometers of the target. Near-field systems are based on emitting light through a microscopic aperture with dimensions smaller than the wavelength of visible light. The emitted light reflects off the closely positioned target and is detected before the light has time to diffract and dissipate. A near-field system may be useful for imaging individual cells or molecules, but is not suitable for most medical procedures and other dynamic applications, which require a field of view of at least a micron and can not be dependant on precisely positioning a tip within nanometers of a target. Using larger wavelengths to provide a suitable field of view with a near-field system would still require a substantially larger imaging system, which could not be integrated into a multi-function instrument.

The concept of a micro-machined scanning optical microscope has also been explored in the form of confocal scanning microscope designs that employ a resonant XY bimorph stage, a resonant cantilever probe and lens, or at least one resonant micro-mirror. The confocal design for image acquisition has the advantage of spatially filtering the backscattered light while using the same optical fiber for illumination and signal collection. However, the extremely low efficiency of light collection (into the core diameter, typically few microns) of this design remains a disadvantage. Furthermore, confocal systems are limited to single wavelength operation, which does not enable color imaging or display.

SUMMARY OF THE INVENTION

Embodiments of the present invention are directed to a two-dimensional optical image scanner that eliminates drawbacks associated with traditional imaging systems. In embodiments of the present invention, the bundle of optical fibers and cameras are eliminated. The scanner offers a sensitive and accurate method to capture high-resolution images of physical and biological tissues. The minute physical size of such an electro-optical imaging system also offers a much needed advantage over conventional imaging systems. Embodiments may provide clinical endoscopic imaging and low cost optical scanners that are only a few millimeters long and that fit inside endoscopic tubes with diameters of less than one mm and tip deflection capability of ninety degrees in some embodiments and up to 360 degrees in other embodiments. This size will enable users to examine areas anatomically inaccessible by currently designed endoscopes, reduce collateral damage to tissue, and enable integration of imaging with other functional devices, such as therapy and diagnostic devices, for example.

The scanner according to embodiments of the present invention also may have high resolution and may have better field of view. The scanner also may be able to transmit multiple wavelengths and variable zoom without loss of resolution (large depth of field). This is made possible by the broadband frequency response and voltage control of the electro-optic actuators, such as, for example, actuators made of a material that can be manipulated optically by an applied electromagnetic field, for light beam deflection. The focus adjustment procedure may be significantly simplified due to the voltage control electro-optic lens array system, thus ensuring speedy observation. Optical magnification is also simplified due to the fact that the zoom-in and zoom-out functions are now controlled by the displacement and the line resolution of the voltage controlled beam deflectors.

The scanner according to embodiments of the present invention also may resolve some of the problems that come with mechanical systems, such as mechanical fatigue, non-linear dynamic effects at large fields of view, mechanical instability (no feedback, prompt to ambient vibration), signal drift, and fixed and low spatial resolution. For example, high scanning speeds (gigahertz range) increase spatial resolution in that it provides more lines per scan. SVGA image or greater resolution is easily obtained without increasing the overall design size. In embodiments, the resolution may be much greater than the currently available highest resolution endoscopes that have approximately 850,000-pixels.

Also using a moving cantilever waveguide to accomplish scanning is eliminated because scanning according to embodiments of the present invention may be accomplished by changing index of refraction of the materials in the scanner rather than using a moving waveguide. This means that the illuminating light spot is not dependent on the dynamics of the waveguide. As a result it is easy to predict and control the exact location of the illuminated spot, making image quality not an issue. Also, the maximum scanning frequency is increased, sensitivity to external vibration and thermal variations is reduces, and field of view is improved For some embodiments, the intergrated optical scanner includes a light source, a lens array, and at least one beam deflector. A single beam deflector may provide up to 360 degrees deflection of a beam. If there are two beam deflectors, one may provide horizontal beam deflection and the other may provide vertical beam deflection. Image acquisition optics and a photodetector array also may be disposed in the same substrate. The integrated optical scanner may be made of electro-optic polymer or liquid crystal polymer.

For some embodiments, a light beam is incident on the integrated optical scanner. The light source may provide a light beam to the lens array. The lens array may have a concave and convex design to focus the light beam to a predetermined size and collimate the focused onto the beam deflector.

For some embodiments, the horizontal beam deflector may include at least two prisms. One prism may have a geometry that is different from the geometry of the other prism such that the first prism encountered by an incident light beam bends the light beam at a first angle and the second prism encountered by the first-bent light beam bends the first-bent light beam at a second angle. The different sizes and shapes of the prisms allow index of refraction for the prisms to be different. The changes in index of refraction permit the difference between the exit angle and the angle of incidence for the scanner to be much greater than if the prisms had identical sizes and shapes.

The prisms may be free standing in that there may be an air gap between each prism. The air gap changes the index of refraction the light beam experiences as it moves from prism to prism. The changes in index of refraction permit the difference between the exit angle and the angle of incidence for the scanner to be much greater than if there were no air gaps between the prisms.

The horizontal beam deflector may be operated passively or actively. For active operation, the angle of incidence may be fixed and a voltage is applied to the prisms to change the index of refraction of the prism material, which causes the light beam to bend in a scanning motion. The prism material can be electro-optic liquid crystal, an optically transparent polymer, etc.

For passive operation, the angle of incidence may not be fixed and a voltage may not be applied to the prisms. The change the index of refraction of the prism may be due to the differing geometries and the air gap(s). The prism material can be glass, plastic, etc.

The vertical beam deflector may be a Bragg grating. Light from the horizontal beam deflector may be coupled to the vertical beam deflector. The Bragg grating may have a near-Gaussian profile such that light diffracted from the Bragg grating may have a Gaussian or near-Gaussian shape.

A third prism may be positioned proximate to the Bragg grating, such as in an opening in the optical packaging formed on top of the Bragg grating, for example. The third prism may help to improve beam deflection in the vertical direction by further bending the light beam in the vertical direction. The third prism and the Bragg grating may be separated by air.

Backscatter from the Bragg grating may be detected by the photodetector array. A spherical lens may be positioned proximate to the Bragg grating, such as in an opening in the optical packaging to bend the light from the Bragg grating towards the photodetector array.

The scanner may be fabricated using microelectromechanical systems (MEMS) technology. The use of MEMS fabrication processes also offers advantages in that it allows for the integration of light sources, scanners, sensors, detectors, and electronics on a single chip configuration. This reduces the overall size and the power consumption of the system, while improving the signal to noise ratio, bandwidth and image quality. Batch processing also enables the production of a high quality product at low cost. This opens the door for design of disposable surgical imaging devices.

A controller may cause the input power supply to drive the horizontal and vertical beam deflectors in a pattern relative to the target so as to display an image on the target and acquire an image of the target.

The scanner may be packaged in a biocompatible material, such as silicone rubber or polydimethylsiloxane (PDMS). The package may include a place for disposing the spherical lens and a place for disposing the third prism. For some embodiments, the scanner may be placed in a holder in which PDMS is poured. A stamp having a pattern may be pressed onto the PDMS. The pattern may include a protrusion for making a depression in the PDMS to accommodate the spherical lens. The pattern alternatively or additionally may include a protrusion for making a depression in the PDMS to accommodate the third prism. The pattern may include a protrusion for making a hole in the PDMS to accommodate the wires for coupling electrical signals to the scanner.

Future portable endoscope systems may be made possible by the proposed integrated image system. With this system, an endoscopic procedure will be performed without sedation of the patient and will be operated from a laptop or a portable monitoring system. Physicians may also be able to examine patients in emergency field settings.

Although embodiments of the present invention are described with reference to a scanner being part of an endoscope used to observe the human body, embodiments are not so limited. For example, the scanner may form part of any application that requires viewing of difficult to access places, such as inside engines, for example, forensic applications, and building inspections. In these embodiments, the packaging may not be biocompatible. Instead, the packaging may be any suitable material that may be shaped and molded.

BRIEF DESCRIPTION OF THE DRAWINGS

In the drawings, like reference numbers generally indicate identical, functionally similar, and/or structurally equivalent elements. The drawing in which an element first appears is indicated by the leftmost digit(s) in the reference number, in which.

DETAILED DESCRIPTION OF THE ILLUSTRATED EMBODIMENTS

Figure 1:
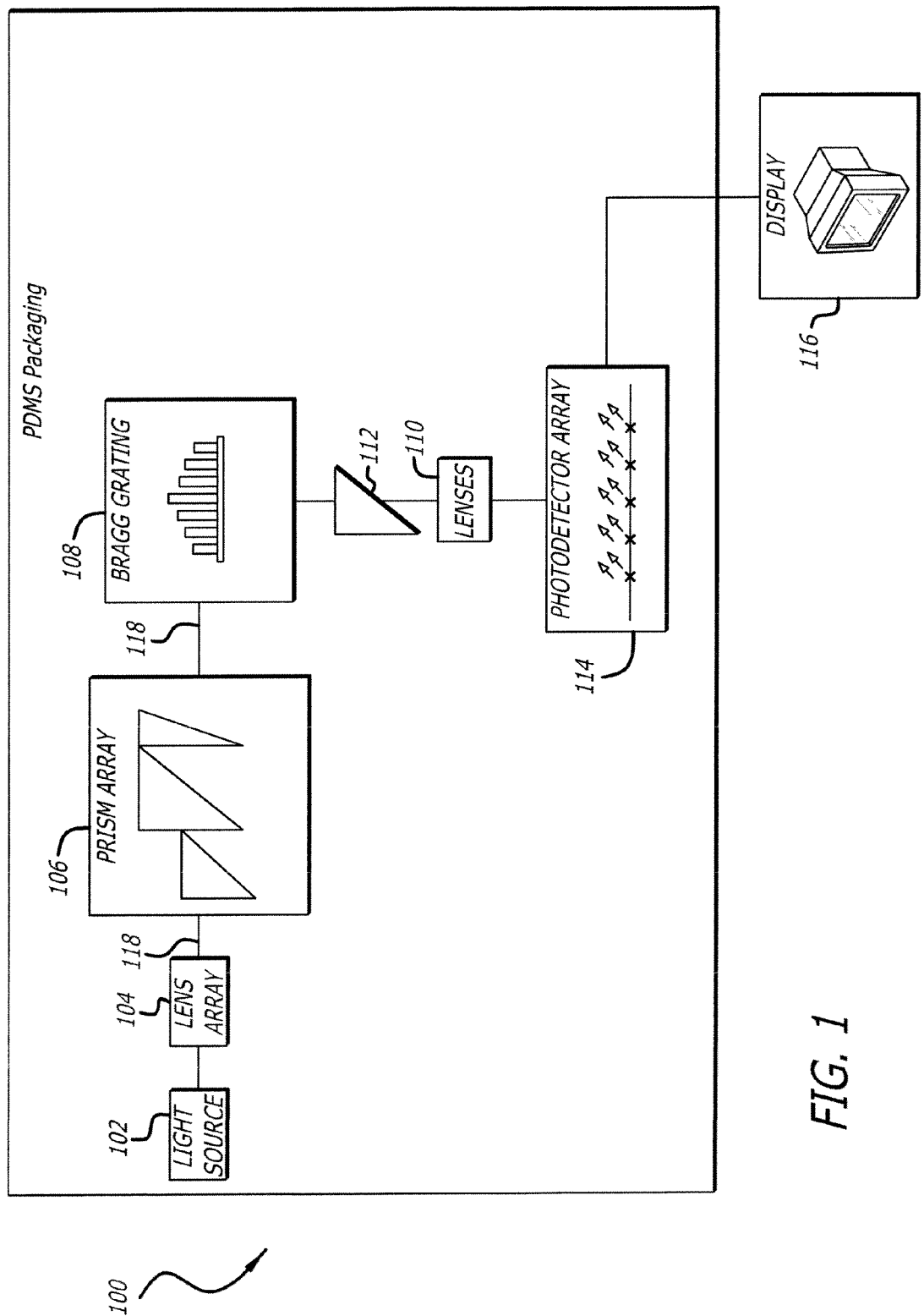
FIG. 1 is a block diagram of a two dimensional electro-optic scanner according to an embodiment of the present invention.

FIG. 1 is a block diagram of an electro-optic scanner 100 according to an embodiment of the present invention. In the illustrated embodiment, the scanner 100 includes a light source 102 coupled to a lens array 104. The lens array 104 is coupled to a prism array 106, which is coupled to a Bragg grating 108. The Bragg grating 108 is optionally coupled to a prism 112, which is optionally coupled to a spherical lens 110. The Bragg grating 108 also may be coupled to a photodetector array 114 without going through the lens 110 and/or the prism 112. The photodetector array 114 is coupled to a display 116. Also in the illustrated embodiment, the light source 102, lens array 104, prism array 106, Bragg grating 108, lens 110, prism 112, and photodetector array 114 are packaged in a biocompatible material such as silicone rubber, dimethicone and/or polydimethylsiloxane (PDMS). Alternatively, the light source 102, lens array 104, prism array 106, Bragg grating 108, lens 110, prism 112, and photodetector array 114 are packaged in other suitable material.

For some embodiments, the light source 102, lens array 104, prism array 106, Bragg grating 108, and photodetector array 114 may be disposed on a waveguide 118 and integrated into the same integrated circuit or chip. This arrangement may be referred to as an optical device. For other embodiments, the optical device includes the lens array 104, prism array 106, Bragg grating 108, and photodetector array 114 may be disposed on the waveguide 118 and integrated into the same integrated circuit and the light source 102 as a pigtail light source is coupled to the chip.

For some embodiments, the display 116 may be any suitable device capable of presenting acquired images visually and perhaps tactilely, such as a video monitor, computer display, or the like.

Figure 2:
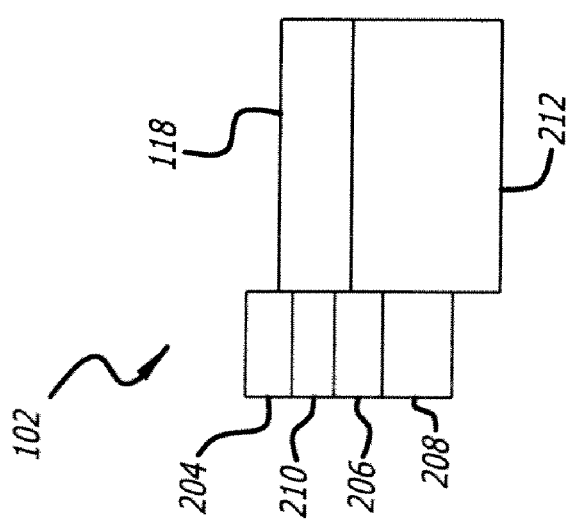
FIG. 2 is a perspective diagram of coupling of light into an optical device according to an embodiment of the present invention.

For some embodiments, the light source 102 may be a semiconductor laser diode. FIG. 2 shows an embodiment of the waveguide 118 and one way in which the light source 102 may be coupled to the waveguide 118 according to an embodiment of the present invention. In the illustrated embodiment, the light source 102 is a semiconductor laser diode having a light emitting layer 202 coupled between a layer of p-type material 204 and a layer of n-type material 206. The layer of n-type material may be disposed on a substrate 208. The waveguide 118 may include a core 210 and a substrate 212. The core 210 may or may not be made for electro-optic material whose optical characteristics, such as index of refraction, change in response to an applied voltage. The substrate 212 may be silicon or other suitable base.

The light source 102 may be end-butt coupled to the waveguide 118. This type of coupling may be suitable to efficiently couple an un-collimated divergent laser beam (10 to 20°) emitted from a semiconductor laser diode, perhaps one that is unpackaged, for example. For some embodiments, the thickness of the waveguide core 210 may be approximately equal to that of the light emitting layer 202. The light emitting layer 202 may be aligned with the waveguide core 210 as shown in FIG. 2. The field distribution of the fundamental lasing mode also may be matched to the TE00 transverse electric waveguide mode. The efficiency may be further improved if indices of refraction of the light emitting layer 202 and the waveguide core 210 are close to each other and the ratio of the thickness of waveguide core 210 to the light emitting layer 202 is small. Index matching epoxy may be used to match the indices of refraction of the light emitting layer 202 and the waveguide core 210 to each other.

For some embodiments, the light source 102 also may be a typical GaAs based heterostructure laser diode. In the fabrication of the light source 102 according to this embodiment, the anomalously fast diffusion of Zn in GaAs is utilized to form a diffused p-n junction lying one to two micrometers below the $Ga_{(1-x)}Al_xAs$ layer and n type GaAs heterojunction. Optical confinement occurs only on one side of the light emitting junction, at the interface between the p type GasAs layer and $Ga_{(1-x)}Al_xAs$ layer. Top and bottom metal electrode layers may provide the contact points between the laser diode and the power supply.

Figure 3:
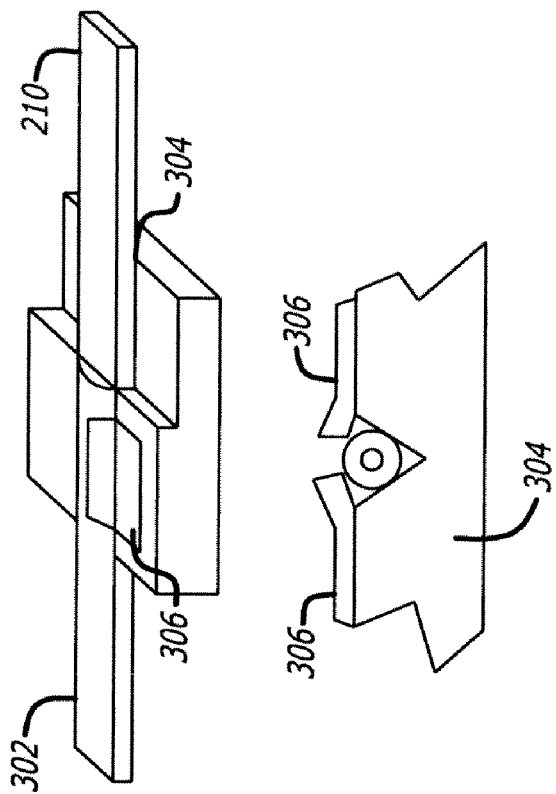
FIG. 3 is a perspective diagram coupling of light into an optical device according to an alternative embodiment of the present invention.

For other embodiments, the light source 102 may be a pigtail laser. In embodiments in which the light source 102 may be a pigtail laser, the light source 102 may be coupled to the waveguide 118 as shown in FIG. 3. In this embodiment, an optical fiber 302 may couple light to the waveguide core 210. A silicon V groove 304 having silicon nitride clips 306 may be used to couple the optical fiber 302 to the waveguide core 210 instead of glue or metal welding. Without gluing or welding, the optical fiber 302 may easily sit in the V groove 304. The V groove 304 may be made from silicon that is by wet etched and may be held in place by the set of silicon nitride clips 306, which are typically manufactured by vapor deposition and wet etching.

In embodiments in which the light source 102 may be a semiconductor laser diode, the output of the light source 102 may diverge when the light is emitted through the aperture defined by the small PN junction. The diffraction that happens at the narrow junction causes the beam to spread into a broader angle. The emission from a GaAs laser diode, for example, tends to be an elliptical beam with a divergence angle around 20° in the direction perpendicular to the PN junction and around 5° in the direction parallel to the PN junction. These angles may vary considerably with individual lasers.

Figure 4:
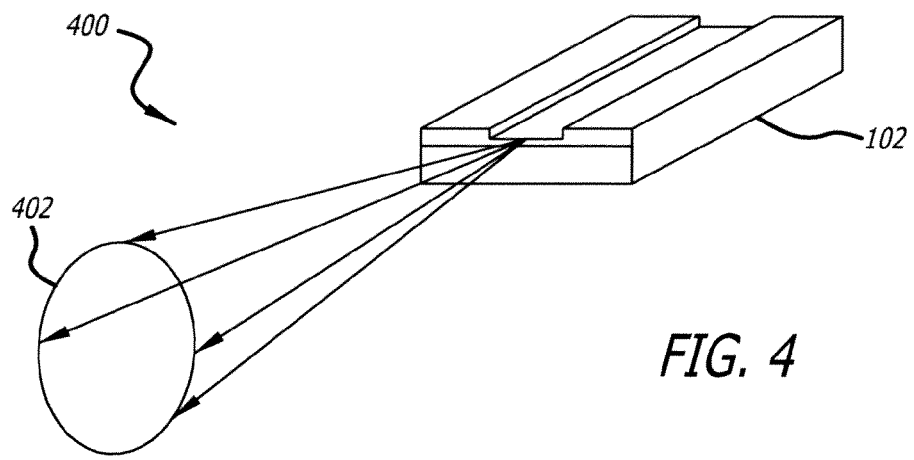
FIG. 4 is a perspective diagram showing a beam profile from a stripe geometry heterojunction GaAs laser according to an embodiment of the present invention.
Figure 5:
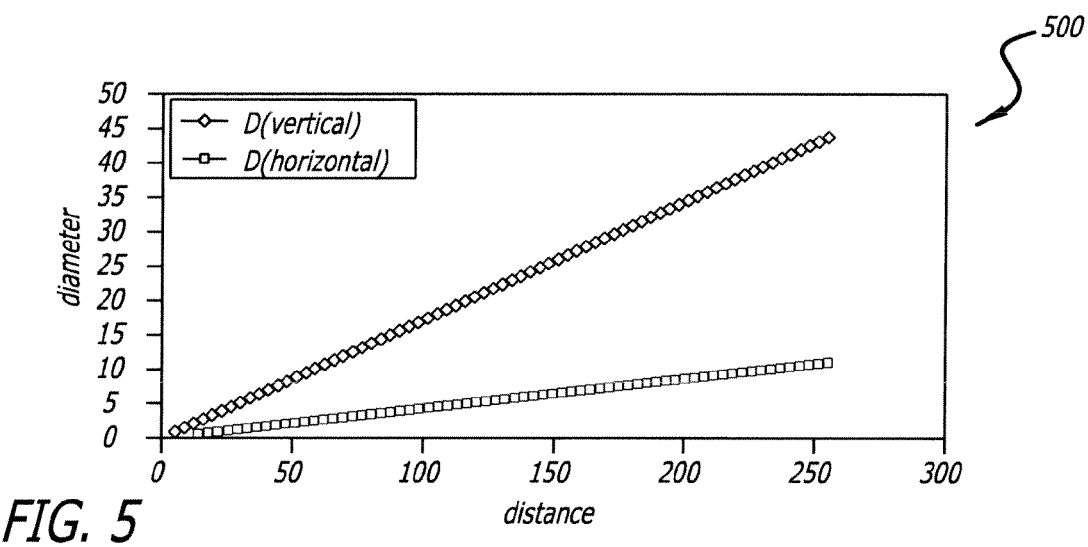
FIG. 5 is a graphical representation showing divergence of the beam from the stripe geometry heterojunction gallium arsenide laser in both vertical and horizontal direction according to an embodiment of the present invention.

FIG. 4 is a perspective diagram showing a beam profile 402 from a stripe geometry heterojunction GaAs laser according to an embodiment of the present invention. FIG. 5 is a graphical representation 500 showing divergence of the beam from the stripe geometry heterojunction gallium arsenide laser in both vertical and horizontal direction according to an embodiment of the present invention. Because the horizontal and vertical divergences are different, for some embodiments the lens array 104 may be a series of convex and concave lenses that collimate and focus the light beam coming from the light source 102 before coupling the light beam to the prism array 106. The material used for the lens array 104 may be electro-optic material such that light refraction through the lens array 104 may be controlled by applying a voltage to the lens array 104.

Figure 6:
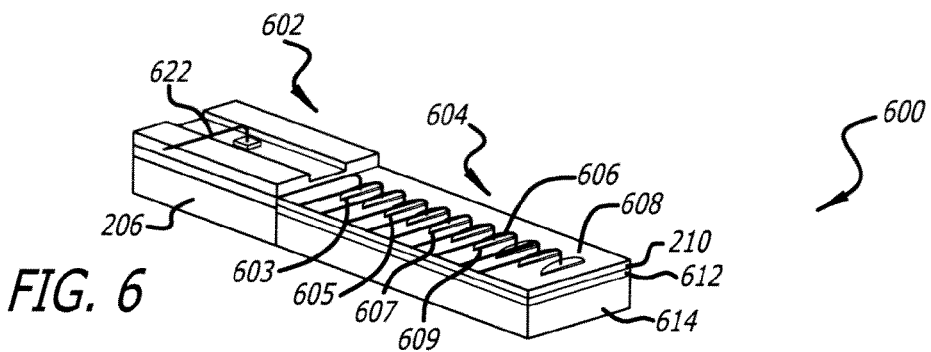
FIG. 6 is a perspective view of an example of how to couple a semiconductor laser diode to a series of plano-convex lenses according to an embodiment of the present invention.

FIG. 6 is a perspective view of an example of how to couple the light source 102 that is a semiconductor laser diode to the lens array 104 according to an embodiment of the present invention. The lens array 104 includes several lenses 603, 605, 607, 607, etc., each having a lens electrode 606 for receiving a voltage to change the index of refraction so that the amount of focusing and collimating can be controlled. The individual lenses 603, 605, 607, 607, etc., are disposed in or on the core 210 of the waveguide 118 and sandwiched between a layer of cladding 612 and a layer of cladding 614. Note that the light source 102 includes the active or light emitting layer 202 sandwiched between the layer of n-type material 206 and the layer of p-type material 204. A metal electrode 622 is disposed on the layer of p-type material 204. The metal electrode 622 may be lens shaped and deposited on the electro-optic polymer core 210.

To properly collimate a light beam using a single plano-convex lens according to an embodiment of the present invention, the index of refraction at the spherical boundary of the lens and the separation between the light source and the lens (or free space encountered by the light beam before encountering the lens) may be determined by:

$$\theta_2 = \theta_1\left(1 - \frac{(n_2 - n_1)d}{n_1 R}\right) - \left(\frac{(n_2 - n_1)y_1}{n_1 R}\right)$$
$$= 0 \Rightarrow \frac{(n_2 - n_1)d}{n_1 R}$$
$$= 0 \Rightarrow R = \frac{(n_2 - n_1)d}{n_1 R}$$

where $\theta_2$ represents the output angle for the light beam, $\kappa_1$ represents the input angle for the light beam, $n_1$ represents the index of refraction of the medium the incident light beam encounters, $n_2$ represents the index of refraction of the planar convex lens, $y_1$ represents_vertical position of the incident light beam at the air/lens interface, R represents the radius of curvature of the planar convex lens, and d represents the separation between the light source and the lens (or free space encountered by the light beam before encountering the lens).

For some embodiments, the separation between the light source and the lens d must equal 100 times of the radius of curvature of the lens, R. The fact is that the larger the separation between the light source and the lens d is the more divergence the light beam has. The radius of the curvature of the lens, R has to be increased to cover the whole divergent light beam. Also, the ratio between the separation between the light source and the lens d and the index of refraction $n_2$ may have to be within a certain reasonable range for proper functioning of the lens.

In the embodiment illustrated in FIG. 6, a series of plano-convex lenses are used instead of a single plano-convex lens. The lenses may be made of electro-optic thin film. The light may be collimated in the horizontal direction of the scanner. The light beam may be kept from diverging more in the vertical direction after exiting the light source 102 by trapping the light in the vertical direction. For this trapping to occur, the incident angle in the vertical direction must be entering the electro-optic thin film less than the total internal reflection, θ, (TIR) angle of an electro-optic thin film waveguide. In this case, the TIR angle may be given by:

$$\theta = \sin^{-1}\left(\frac{n_0}{n_{eo}}\right) = \sin^{-1}\left(\frac{1}{1.6}\right) = 38.68°$$

where $n_0$ is the index of refraction of air and $n_{eo}$ is the index of refraction of the electro-optic thin films. If the light source 102 comes from a single mode optical fiber, based on indices of a single mode fiber, the incident angle of the diverging light beam to the first collimating electro-optic lens may be approximately eighty degrees. In this instance, light in the vertical direction may be completely confined based on the TIR angle condition. The angle of incidence to the consequent lens system in the vertical direction must be calculated to find out the actual light coupling in the vertical direction. The angle of incidence is defined by the TIR angle condition.

Using the matrices transfer methods, the output angle for a given point source may be calculated. To make it simple, the types of lens and separations between the light source and individual lenses may be substantially the same. In this manner, the same calculations may be used for all the lenses in the lens array 104 illustrated in FIG. 6. The types of lenses and their separations may be determined by the following equation:

$$\theta_2 = \theta_1\left(1 - \frac{(n_2 - n_1)d}{n_1 R}\right) - \frac{(n_2 - n_1)y_1}{n_1 R} = 0$$

$$\Rightarrow 1 - \frac{(n_2 - n_1)d}{n_1 R} = 0$$

$$\Rightarrow R = \frac{(n_2 - n_1)d}{n_1}$$

where $\theta_2$ represents the output angle for the light beam, $\theta_1$ represents the input angle for the light beam, $n_1$ represents the index of refraction of the first plane boundary of the lens encountered by the light beam, $n_2$ represents the index of refraction of the second plane boundary of the lens encountered by the light beam, $y_1$ represents the vertical position of the incident light beam on the lens, R represents radius of curvature of the lens, and d represents the separation between the light source and the lens and between individual lenses (or free space encountered by the light beam before encountering a lens). For some embodiments, the radius of the lenses R may be 80 micrometers and the number of lenses and the ratio of the distance between the light source and the lens and between individual lenses d/R may vary. A smaller ratio of the distance between the light source and the lens and between individual lenses d/R may produce a light beam having less divergence than with a ratio of the distance between the light source and the lens and between individual lenses d/R.

In one embodiment, the number of lenses may be sixteen and the ratio of the distance between the light source 102 and the first lens 603 and between individual lenses d/R may be 0.8.

In another embodiment, the index of refraction of the second plane boundary of the lens encountered by the light beam $n_2$ may be 1.608, the index of refraction of the first plane boundary of the lens encountered by the light beam $n_1$ may be 1, the radius of a lens R may be 0.608(d), the distance between the light source and the lens and between individual lenses d may be 200 micrometers and thus the radius of a lens R may be 121.6 micrometers. The ends of an individual lens may be trimmed so that the lens has a height h of 80 micrometers, a distance between the light source and the lens and between individual lenses d of 199.6 micrometers, a lens thickness T and a radius R of 121.8 micrometers.

In another embodiment, there may be ten lenses in the lens array 104 depicted in FIG. 6. In this embodiment, the ratio of the distance between the light source 102 and the first lens 603 and between individual lenses d/R may be 1.95 wherein the radius R is eighty micrometers and the distance between the light source and the lens and/or between individual lenses d is 1.95. The thickness of an individual lens may less than eight micrometers.

Figure 7:
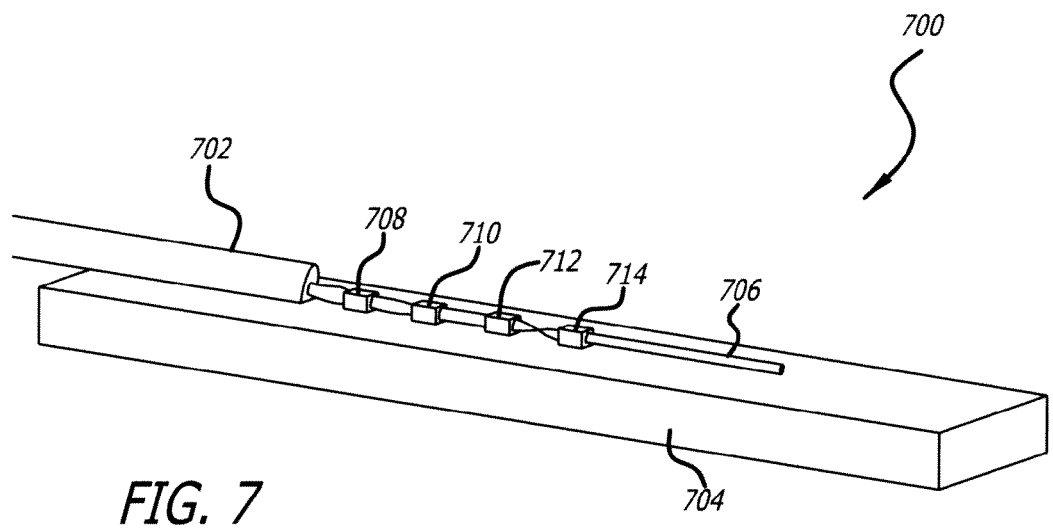
FIG. 7 illustrates a lens array that may collimate and focus a light beam according to an embodiment of the present invention.

FIG. 7 illustrates a lens array 104 that may collimate and focus a light beam (reduce the size of the light beam) according to an alternative embodiment of the present invention. In this embodiment, the lens array 104 includes a series of convex and concave lenses of varying sizes to collimate and focus the light beam before coupling the light beam to the prism array 106.

Figure 8:
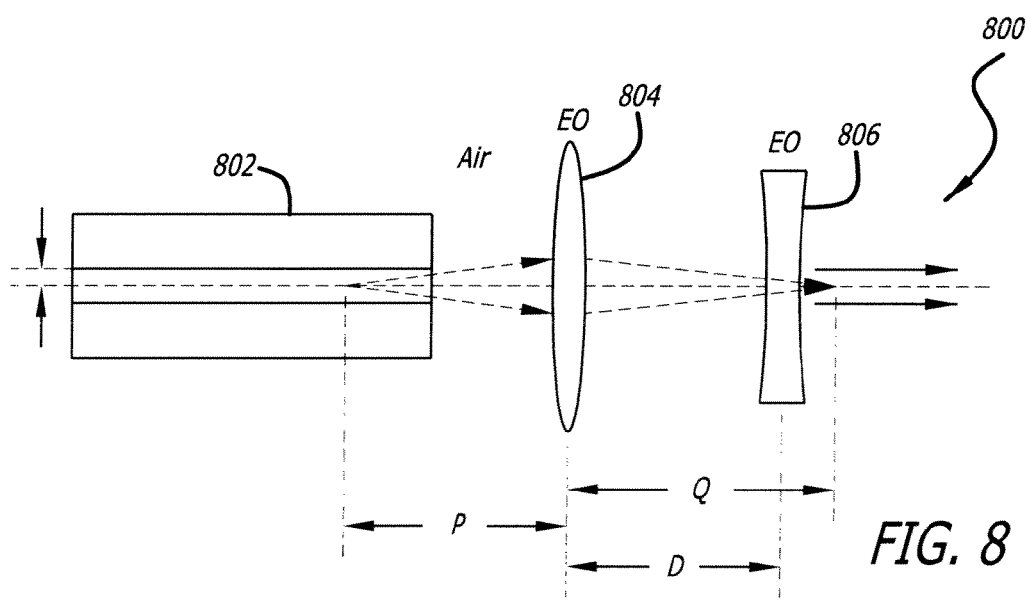
FIG. 8 is a diagram showing a two-dimensional light path via a convex-concave array of lenses according to an embodiment of the present invention.

In the illustrated embodiment, the lens array 104 includes an optical fiber 702 having cladding (not labeled) and a core 706. The lens array 104 is coupled to a substrate 704 and the fiber core 706. The lens array 104 includes several lenses 708, 710, 712, and 714 also are disposed on the substrate 704 and coupled to the fiber core 706. FIG. 7 may be described further using FIG. 8, which is a diagram showing a two-dimensional light path via a convex-concave array 800 of lenses according to an embodiment of the present invention. In FIG. 8, an optical fiber 802 couples light through air to a (bi)convex lens 804 that couples light through air to a (bi)concave lens 806. In embodiments in which the lens 804 and 806 are thin lenses in which the thickness or distance along the optical axis between the two surfaces of the lens is negligible compared to the focal length of the lens, the governing equations may be as follows:

$$\frac{1}{P} + \frac{1}{Q} = \frac{1}{f_1} = (n-1)\left(\frac{1}{R_1} - \frac{1}{R_2}\right)\langle R_1: +\ R_2: -\rangle$$

$$Q - D = f_2 = \frac{1}{(n-1)\left(\frac{1}{R_3} - \frac{1}{R_4}\right)}\langle R_3: -\ R_4: +\rangle$$

where P represents image length, Q represents objective length, $f_1$ represents the focal point of the lens 804, n represents the refractive index of the concave lens 804, $R_1$ represents the radius of the convex lens 804, $R_1$: represents the radius of the curvature of the front surface of the convex lens 804, $R_2$: represents the radius of the curvature of the back surface of the convex lens 804. D represents the distance separating the convex lens 804 and the concave lens 806, $f_2$ represents the focal point of the concave lens 806, $R_3$ represents the radius of the curvature of the front surface of the concave lens 806, and $R_4$ represents the radius of the curvature of the back surface of the concave lens 806. Also, one-half of the height of the lens H is greater than the radius of the diverged light beam $R_{cone}$ (H/2>$R_{cone}$) and the ratio of the height of the lens H to the thickness of the lens W (H/W) may be relatively large to ensure the lens is a thin lens rather than a thick lens. Then, by defining the P, D and one of the focal lengths (or radii), the other focal length may be determined.

Another approach to designing a lens array according to embodiments of the present invention may use ray-transfer matrices as follows.

$$M = \begin{pmatrix} 1 & 0 \\ -\frac{1}{f_2} & 1 \end{pmatrix} * \begin{pmatrix} 1 & d_2 \\ 0 & 1 \end{pmatrix} * \begin{pmatrix} 1 & 0 \\ -\frac{1}{f_1} & 1 \end{pmatrix} * \begin{pmatrix} 1 & d_1 \\ 0 & 1 \end{pmatrix}$$

$$= \begin{pmatrix} 1 & d_2 \\ -\frac{1}{f_2} & 1 - \frac{d_2}{f_2} \end{pmatrix} * \begin{pmatrix} 1 & 0 \\ -\frac{1}{f_1} & 1 \end{pmatrix} * \begin{pmatrix} 1 & d_1 \\ 0 & 1 \end{pmatrix}$$

$$= \begin{pmatrix} 1 - \frac{d_2}{f_1} & d_2 \\ -\frac{1}{f_2} - \frac{1}{f_1}\left(1 - \frac{d_2}{f_2}\right) & 1 - \frac{d_2}{f_2} \end{pmatrix} * \begin{pmatrix} 1 & d_1 \\ 0 & 1 \end{pmatrix}$$

$$= \begin{pmatrix} 1 - \frac{d_2}{f_1} & d_2 + d_1\left(1 - \frac{d_2}{f_1}\right) \\ -\frac{1}{f_2} - \frac{1}{f_1}\left(1 - \frac{d_2}{f_2}\right) & 1 - \frac{d_2}{f_2} - \frac{d_1}{f_2} - \frac{d_1}{f_1}\left(1 - \frac{d_2}{f_2}\right) \end{pmatrix}$$

where $f_1$ represents the focal point of the first lens, $f_2$ represents the focal point of the second lens, $d_1$ represents the distance between the light source and the first lens, $d_2$ represents the distance between the two lenses. For the beam to be collimated, the output angle $\theta_2$ of the array 800 may equal 0 for any input angle $\theta$. If $y_1=0$, then:

$$\begin{bmatrix} y_2 \\ \theta_2 \end{bmatrix} = M * \begin{bmatrix} y_1 \\ \theta_1 \end{bmatrix}$$

$$= \begin{pmatrix} 1 - \frac{d_2}{f_1} & d_2 + d_1\left(1 - \frac{d_2}{f_1}\right) \\ -\frac{1}{f_2} - \frac{1}{f_1}\left(1 - \frac{d_2}{f_2}\right) & 1 - \frac{d_2}{f_2} - \frac{d_1}{f_2} - \frac{d_1}{f_1}\left(1 - \frac{d_2}{f_2}\right) \end{pmatrix} * \begin{bmatrix} y_1 \\ \theta_1 \end{bmatrix}$$

$$= \begin{bmatrix} \left(1 - \frac{d_2}{f_1}\right)*y_1 + \left(d_2 + d_1\left(1 - \frac{d_2}{f_1}\right)\right)\theta_1 \\ \left(-\frac{1}{f_2} - \frac{1}{f_1}\left(1 - \frac{d_2}{f_2}\right)\right)y_1 + \theta_1\left(1 - \frac{d_2}{f_2} - \frac{d_1}{f_2} - \frac{d_1}{f_1}\left(1 - \frac{d_2}{f_2}\right)\right) \end{bmatrix}$$

$$\theta_1\left(1 - \frac{d_2}{f_2} - \frac{d_1}{f_2} - \frac{d_1}{f_1}\left(1 - \frac{d_2}{f_2}\right)\right) = 0$$

$$\Rightarrow 1 - \frac{d_2}{f_2} - \frac{d_1}{f_2} - \frac{d_1}{f_1}\left(1 - \frac{d_2}{f_2}\right) = 0$$

$$\Rightarrow f_1 f_2 - f_1 d_2 - f_1 d_1 - f_2 d_1 + d_1 d_2 = 0$$

$$f = \frac{1}{(n-1)\left(\frac{1}{R_1} - \frac{1}{R_2}\right)}$$

where $y_1$ is the vertical position of the point of incidence of the light beam, $\theta_1$ is the incident angle of the light beam, $Y_2$ is the existing vertical position, and $\theta_2$ is the existing angle.

Table 1 below describes two sets of parameters for the arrangement 800 for collimating and focusing a point source light beam according to embodiments of the present invention.

TABLE 1 units: microns

| | Lens # (Type) | | | |
|---|---|---|---|---|
| | 804 (Convex) | 806 (Concave) | 804 (Convex) | 806 (Concave) |
| $R_1$ | 120 | −150 | 182 | −160 |
| $R_2$ | −120 | 150 | −182 | 160 |
| f | 98.6842105 | −123.355263 | 149.671053 | −131.5789474 |
| $d_1$ | 150 | | 250 | |
| $d_2$ | 165.106275 | | 241.371872 | | where $d_1$ represents the distance between the light source and the lens 804, $d_2$ represents the distance between the lens 804 and the lens 806, f represents the focal points of the respective lenses 804 and 806, $R_1$ represents the radius of curvature of front surface of the respective lenses 804 and 806, and $R_2$ represents the radius of curvature of the back surface of the respective lenses 804 and 806.

Figure 9:
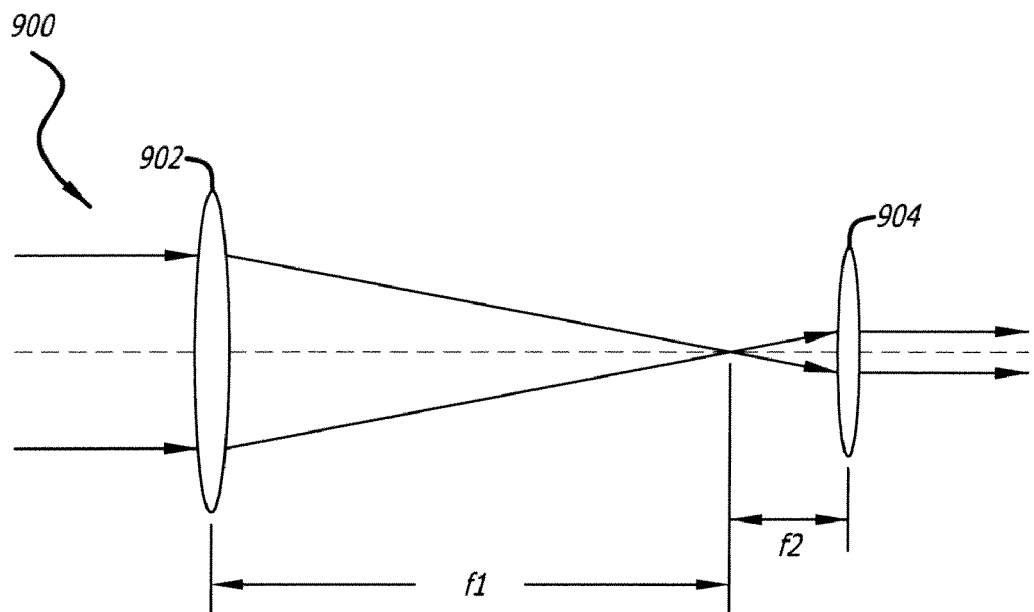
FIG. 9 is a diagram showing a two-dimensional light path via a convex-convex combination of thin lenses according to an embodiment of the present invention.

FIG. 9 is a diagram showing a two-dimensional light path via a convex-convex combination of thin lenses 902 and 904 according to an embodiment of the present invention. In the illustrated embodiment, $f_1$ represents the focal point of the lens 902 and $f_2$ represents the focal point of the lens 904. The behavior of the lens array 104 according to this embodiment can be characterized by the following:

$$D = f_1 + f_2$$

$$f_i = \frac{1}{(n-1)\left(\frac{1}{R_1} - \frac{1}{R_2}\right)}$$

where D represents the distance between the lens 902 and the lens 904, n represents_index of refraction of the lens_, $f_1$ represents the focal point of the lens 902, $f_2$ represents the focal point of the lens 904, $f_i$ represents the general focal length equation, i represents the lens number, n represents the_index of refraction of the particular lens, $R_1$ represents the radius of curvature of front surface of the respective lenses 902 and 904, and $R_2$ represents the radius of curvature of back surface of the respective lenses 902 and 904. Also, one-half of the height of each lens H is greater than the radius of the diverged light beam $R_{cone}$ (H/2>Rcone) and the ratio of the height of the lens H to the thickness of the lens W (H/W) may be relatively large to ensure an individual lens is a thin lens rather than a thick lens.

Table 2 below describes two sets of parameters for the arrangement 900 for focusing a light beam according to alternative embodiments of the present invention.

TABLE 2 units: microns

| | Lens # (Type) | | | |
|---|---|---|---|---|
| | 902 (Convex) | 904 (Convex) | 902 (Convex) | 904 (Convex) |
| $R_1$ | 180 | −100 | 152 | −75 |
| $R_2$ | −180 | 100 | −152 | 75 |
| f | 148.026316 | 82.2368421 | 125 | 61.67763158 |
| D | 230.263158 | | 186.677632 | | where D represents the distance between the lens 902 and the lens 904, f represents the focal points of the respective lenses 902 and 904, $R_1$ represents the radius of curvature of front surface of the respective lenses 902 and 904, and $R_2$ represents the_radius of curvature of back surface of the respective lenses.

Table 3 below describes parameters for an arrangement of four lenses that collimate and focus a light beam according to an embodiment of the present invention.

TABLE 3 units: microns

| | Lens Type | | | |
|---|---|---|---|---|
| | Convex | Concave | Convex | Convex |
| $R_1$ | 120 | −150 | 180 | −100 |
| $R_2$ | −120 | 150 | −180 | 100 |
| f | 98.6842105 | −123.355263 | 148.026316 | 82.23684211 |
| T | 10 | 5 | 10 | 10 |
| D | 150 | 165.106275 | 200 | 230.2631579 | where D represents the distance of the lens from the light source, f represents the focal points of the respective lenses, $R_1$ represents the radius of curvature of front surface of the respective lenses 902 and 904, $R_2$ represents the radius of curvature of back surface of the respective lenses 902 and 904, and T represents the thickness of the respective lenses 902 and 904.

Table 4 below describes parameters for an arrangement of four lenses that collimate and focus a light beam according to an alternative embodiment of the present invention.

TABLE 4 units: microns

| | Lens Type | | | |
|---|---|---|---|---|
| | Convex | Concave | Convex | Convex |
| $R_1$ | 182 | −160 | 152 | −75 |
| $R_2$ | −182 | 160 | −152 | −75 |
| f | 149.671053 | −131.578947 | 125 | 61.6776316 |
| T | 16 | 6 | 8 | 8 |
| D | 348 | 326 | 296 | 142 |
| H | 106.7333 | 86.81014 | 69.28203 | 48.33218 |
| H/T | 6.670832 | 14.46836 | 8.660254 | 6.041523 |
| H(round) | 102 | 80 | 65 | 40 | where D represents the distance of the lens from the light source, f represents the focal points of the respective lenses, $R_1$ represents the radius of curvature of front surface of the respective lenses, $R_2$ represents the radius of curvature of back surface of the respective lenses, T represents the thickness of the respective lenses, H represents the height of the respective lenses, H/T represents the height to thickness ratio of the respective lenses, and H(round) represents the height rounded to whole number of the respective lenses. The rounded number may be the actual dimension used in fabrication because it may be easier for fabrication.

For some embodiments, one or more lenses in the lens array 104 may comprise electro-optic material. In these embodiments, applying an electrical charge to the lenses in the lens array may change the optical characteristics such as the index of refraction of the lenses. Changing the optical characteristics of the lenses may change the amount and angle of deflection of an incident light beam.

Figure 10:
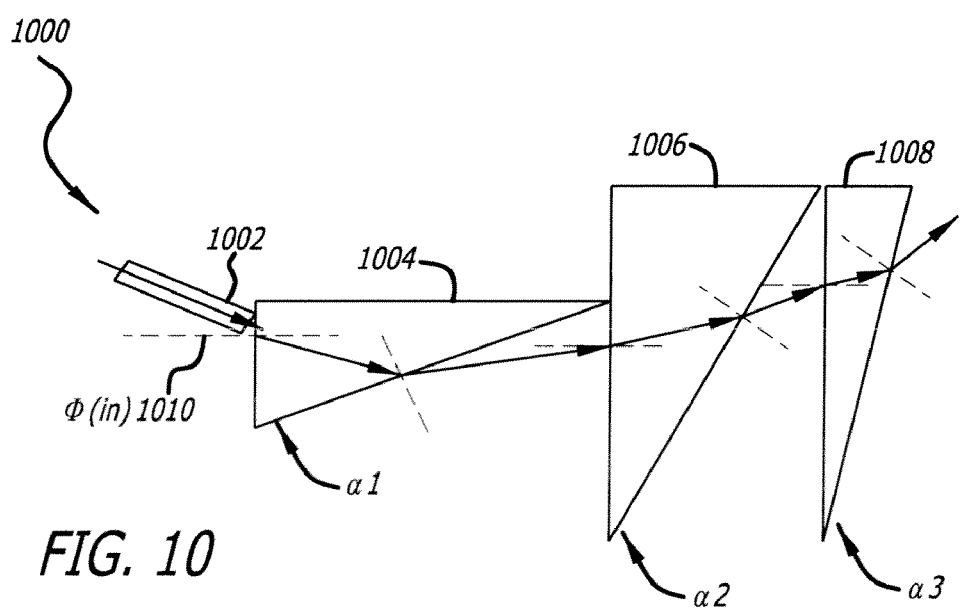
FIG. 10 is a diagram of a two-dimensional light path of an incident ray through a prism array according to an embodiment of the present invention.

As described above, the lens array 104 is operationally coupled to the prism array 106. FIG. 10 is a diagram of a two-dimensional light path of an incident ray through a prism array 1000 suitable for implementing the prism array 106 according to an embodiment of the present invention. In the illustrated embodiment, an optical fiber 1002 is coupled to three prisms 1004, 1006, and 1008 so that an incident light beam 1010 from the optical fiber 1002 can be bent from its angle of incidence Φ(in) to an exit angle. The prism array 106 is a series of free standing prisms of varying shapes, sizes, and geometries such that light traveling between prisms travels through air before encountering each subsequent prism. Although illustrated as right triangles, the prisms in the prism array 106 need not be right triangles. For example, any one of the triangles may be equilateral, isosceles, scalene, obtuse, and/or acute.

For some embodiments, the first prism 1004 bends the light beam 1010 in a first direction, a second prism 1006 bends the light beam 1004 in a second direction. A third prism 1008 bends the light beam 1004 in a third direction. How much the light beam 1010 is bent and in which direction may be determined by the geometry of a specific prism, the angle of incidence Φ(in) of the light beam 1010, the position that the light beam 1010 strikes the input boundaries of the individual prisms, the index of refraction of the individual prisms' material, and the index of refraction at the output boundary of the individual prism.

Figure 11:
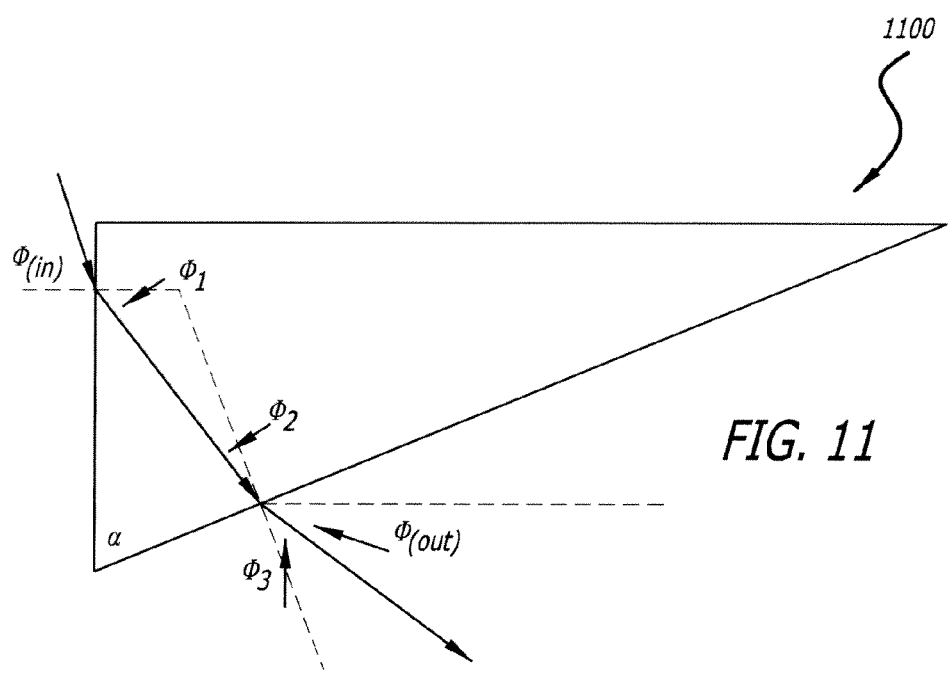
FIG. 11 is a diagram showing a two-dimensional light path via through a right angle prism according to an embodiment of the present invention.

FIG. 11 is a diagram showing a two-dimensional light path via through a right angle prism 1100 according to an embodiment of the present invention. In the illustrated embodiment, the light beam 1010 encounters the input boundary of the prism 1100 at an angle of incidence Φ(in). The light beam 1010 bends at an angle $\Phi_1$ determined by the angle of incidence Φ(in) of the light beam 1010, by the index of refraction at the input boundary $n_{in}$ of the prism 1100, by the index of refraction of the prism 1100 material $n_{prism}$, by the index of refraction at the output boundary $n_{out}$ of the prism 1100, and by the geometry a of the prism 1100.

The relationships of the geometric angles shown in FIG. 11 may be derived as follows:

$$\phi_1 = \sin^{-1}\left(\frac{n_{in}\sin\phi_{in}}{n_{prism}}\right)$$

$$\phi_2 = \alpha - \phi_1$$

$$\phi_3 = \sin^{-1}\left(\frac{n_{prism}\sin\phi_2}{n_{out}}\right)$$

$$\phi_{out} = \text{abs}(\alpha - \phi_3)$$

Figure 12:
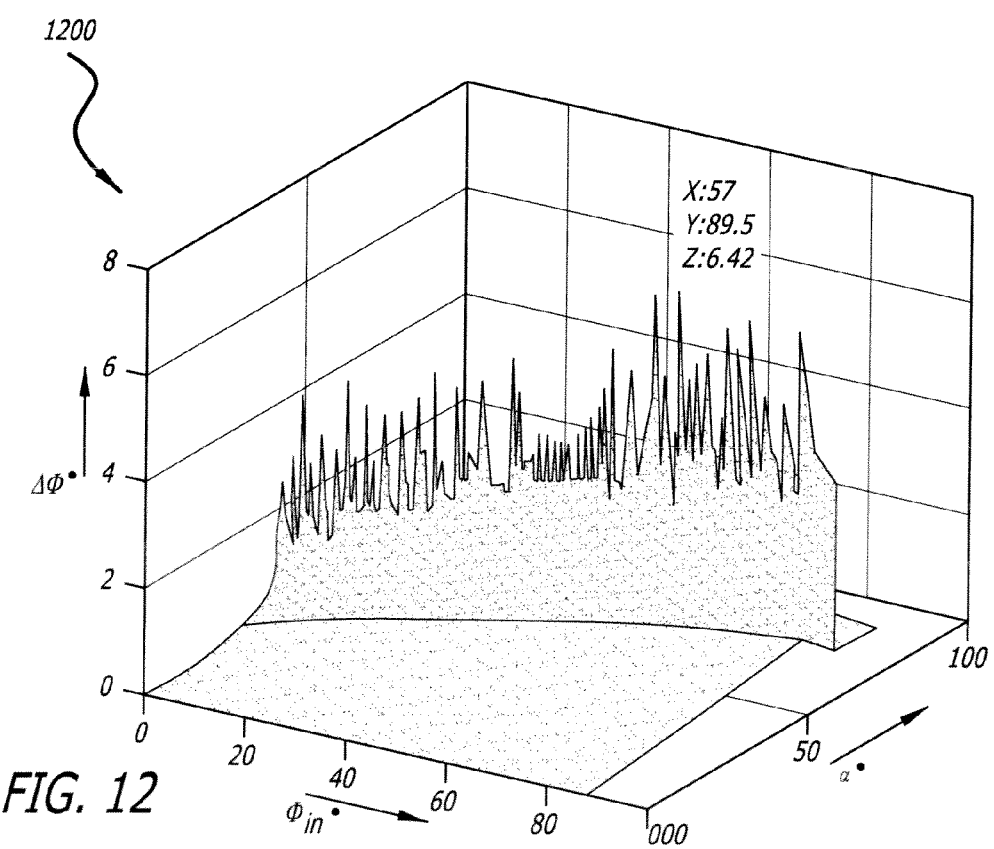
FIG. 12 is a three dimensional plot illustrating the change between the angle of incidence and the output angle of a prism according to an embodiment of the present invention.

FIG. 12 is a three dimensional plot 1200 illustrating the change ΔΦ between the angle of incidence φ(in) and the output angle φ (out) according to an embodiment of the present invention. This change may directly correlate to an amount of horizontal deflection the light beam 1010 undergoes as it passes through the prism 1100. The plot 1200 illustrates the dependence of the amount of deflection Δφ on the geometry α of the prism 1100 and the angle of incidence Φ(in) of the light beam 1010.

Table 5 below describes different possible deflections ΔΦ given various geometries a of the prism 1100 and the angles of incidence Φ(in) of the light beam 1010 according to embodiments of the present invention.

TABLE 5

| Φ(in) (degrees) | α (degrees) | ΔΦ (degrees) |
|---|---|---|
| 57 | 69.5 | 6.42 |
| 61 | 71 | 6.333 |
| 65.5 | 72.5 | 6.287 |

Referring back to FIG. 10, in the illustrated embodiment the prisms 1004, 1006, and 1008 are right triangles each having a different angle of interest. The prism 1004 has angle α1 as an angle of interest, the prism 1006 has angle $\alpha_2$ as an angle of interest, and the prism 1008 has angle $\alpha_3$ as an angle of interest. The angle of interest α1, the incident angle of the light beam 1010 at the prism 1004 input boundary, the position that the light beam 1010 strikes the prism 1004 input boundary, the index of refraction at the input boundary of the prism 1006, and the index of refraction of the prism 1004 material may determine how much the prism 1004 bends the light beam 1010.

The prism 1006 has angle α2 as an angle of interest. The angle of interest α2, the incident angle of the light beam 1010 at the prism 1006 input boundary, the position that the light beam 1010 strikes the prism 1006 input boundary, the index of refraction at the input boundary of the prism 1006, the index of refraction of the prism 1006 material, and the index of refraction at the output boundary of the prism 1006 may determine how much the prism 1006 bends the light beam 1010.

The prism 1008 has angle α3 as an angle of interest. The angle of interest α3, the incident angle of the light beam 1010 at the prism 1008 input boundary, the position that the light beam 1010 strikes the prism 1008 input boundary, the index of refraction at the input boundary of the prism 1008, the index of refraction of the prism 1008 material, and the index of refraction at the output boundary of the prism 1008 may determine how much the prism 1008 bends the light beam 1010.

The different directions may be dependent upon the angle of incidence Φ(in) of the light beam 1010, the position that the light beam 1010 strikes the prism 1004 input boundary, the index of refraction at the input boundary of the prism 1004, the index of refraction of the prism 1004 material, and the index of refraction at the output boundary of the prism 1004 may determine how much the prism 1004 bends the light beam 1010. The angle of interest a2, the incident angle of the light beam 1010 at the prism 1006 input boundary, the position that the light beam 1010 strikes the prism 1006 input boundary, the index of refraction at the input boundary of the prism 1006, the index of refraction of the prism 1006 material, and the index of refraction at the output boundary of the prism 1006 may determine how much the prism 1006 bends the light beam 1010. The angle of interest a3, the incident angle of the light beam 1010 at the prism 1008 input boundary, the position that the light beam 1010 strikes the prism 1008 input boundary, the index of refraction at the input boundary of the prism 1008, the index of refraction of the prism 1008 material, and the index of refraction at the output boundary of the prism 1008 may determine how much the prism 1008 bends the light beam 1010.

For some embodiments, the prisms 1004, 1006, and/or 1008 are free standing optics in that there is air between the surfaces of the prisms 1004, 1006, and/or 1008. In these embodiments, the difference in the index of refraction of the output boundary of a prism and the index of refraction of air is much larger than the difference in the index of refraction of the output boundary of the prism and the index of refraction of another prism. As such, the amount the light beam may be bent going from one prism through air is greater than the amount the light beam may be bent going from one prism substantially directly to another prism or other optical coupler. Snell's law may be used to determine used to how the light beam 1010 may be bent going from the prisms 1004, 1006, and/or 1008 and air.

For some embodiments, the prism array may operate passively. That is, no voltage is applied to the prisms 1004, 1006, and/or 1008. The change in index of refraction that exists between the prisms 1004, 1006, and/or 1008 causes the exit angle to get larger as we move from prism to prism resulting in a large deflection at the output of the prism array 1008. The angle that the light beam 1010 ultimately is deflected is larger than the angle of incidence Φ(in). For this passive operation, the prisms 1004, 1006, and/or 1008 may be glass, plastic, etc. Also, in this embodiment, the angle of incidence Φ(in) may be changing so the exit angle will scan accordingly.

For some embodiments, the prism array 106 may operate actively. That is, a voltage may be applied to the prisms 1004, 1006, and/or 1008 to change the indices of refraction of the prisms 1004, 1006, and/or 1008. The changed indices of refraction of the prisms 1004, 1006, and/or 1008 may cause the amount that the light beam 1010 is bent by a particular prism to change from what the amount of bending would have been had there been no voltage applied to the prisms 1004, 1006, and/or 1008. In this embodiment, the angle of incidence Φ(in) may be fixed (or may change) and the exit angle will scan based on changing the indices of refraction of the prisms 1004, 1006, and/or 1008. For some embodiments, the prisms 1004, 1006, and/or 1008 may be a polymer, such as an optically transparent polymer, for example, an electro-optic material, a liquid crystal material, or other material whose optical properties change in response to an applied voltage. For some embodiments, the prism array illustrated in FIG. 10 may be constructed by adding several layers of electro-optic material.

Table 6 below describes different possible deflections ΔΦ given various geometries α of the prism array 1000 and the angles of incidence Φ(in) of the light beam 1010 according to embodiments of the present invention.

TABLE 6

| Φ(in) (degrees) | α1 (degrees) | α2 (degrees) | α3 (degrees) | ΔΦ (degrees) |
| --- | --- | --- | --- | --- |
| 61 | 71 | 27.4 | 4 | 30.30673 |
| 65.5 | 72.5 | 28.4 | 5.8 | 39.0952 |

Note that having several prisms with different geometries affords much greater deflection ΔΦ of the light beam 1010.

For embodiments in which the prisms 1004, 1006, and/or 1008 are electro-optic polymer films the refractive index of the prism 1004, 1006, and/or 1008 may be changed by applying a voltage across the individual films. The change in index of refraction may further change the amount of deflection ΔΦ of the light beam 1010.

In one embodiment in which the prism array 106 includes liquid crystal material, there may be a single prism. In this embodiment, the prism made from the liquid crystal material may provide up to 360 degrees of deflection of the light beam 1010 from the angle of incidence Φ(in) in response to the applied voltage depending on the sensitization of the liquid crystal and/or the applied voltage. Also, the Bragg grating 108 may be eliminated if the liquid crystal is configured to rotate the light beam 1010 ninety degrees.

Figure 13:
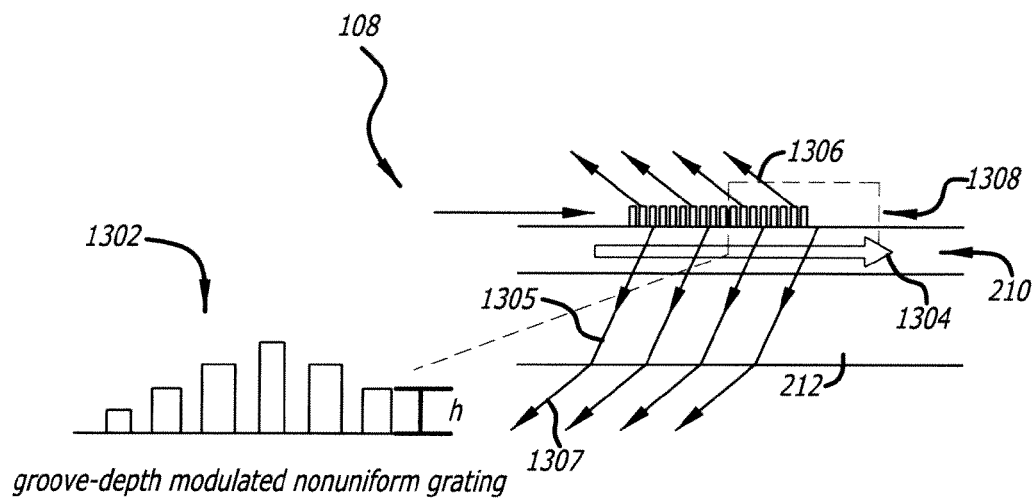
FIG. 13 is a diagram illustrating a Bragg grating according to an embodiment of the present invention.

FIG. 13 is a diagram illustrating the Bragg grating 108 according to an embodiment of the present invention. In the illustrated embodiment, the Bragg grating 108 includes a near-Gaussian profile, indicated by the portion 1302, which gives the light beam 1304 reflected by the Bragg grating 108 a Gaussian profile. The resulting shape of the reflected light beam may be more focused and collimated than without the Gaussian Bragg grating.

The Bragg grating 108 may be viewed as a coupler functioning as a surface-wave to leaky-wave converter. Due to the exponential attention of the guided light beam 1304, the light beam reflected by the Bragg grating 108 exhibits an exponential profile. The equivalent beam $w_{eq}$ is given by:

$$w_{eq} = \frac{1}{\alpha \sec\phi_v}$$

where α represents leakage in the grating region and $\phi_v$ represents the angle of waves radiating into the air region at the gratings. Based on the equation, the leakage α in the grating region is a function of grating depth h. Therefore, as the grating depth increases, the width of the light beam may be reduced. Electron beam lithography or ultraviolet (UV) interference lithography may be used to fabricate linearly tapered sinusoidal gratings having the groove-depth modulated non-uniform Bragg grating depicted in FIG. 1.

In the illustrated embodiment, a light beam 1304 travels through the waveguide core 210 and is coupled to the Bragg grating 108. The Bragg grating 108 reflects the light beam 1306 into the upper air region 1308. Light from the light beam 1304 also leaks from the waveguide core 210 into the substrate 212, as illustrated by the arrows 1305, and from the substrate region 212, as illustrated by the arrows 1307. In one embodiment, the Bragg grating 108 may include an electro-optic polymer.

In one embodiment, the material for the electro-optic polymer may be polystyrene-based Diels-Alder cross-linkable NLO polymers with a TCF-type chromophore thin film. This material provides high electro-optical coefficient, is thermally and photo-chemically stable, and has low loss stemming from absorption, impurity scattering, and surface scattering. The cladding 110 may be made of a material such as Noland 63 UV 15, and Noland 61. The choice for the electrodes for applying a voltage to the Bragg grating 108 is gold deposited thin film.

In embodiments of the invention, a commonly used laser holography technique for sub-micron level lithography may be used for the Bragg grating 108 construction. The Bragg grating 108 structure may be formed by first exposing a 488 nm wavelength (Argon laser) or 325 nm (Helium Cadmium Laser) UV interference pattern on a photosensitive polymer such as positively toned Ultra123 and negatively toned SU-8, (MicroChem Corp., MA) and placed on top of a silicon substrate to form the master. The film may be subsequently developed and have a periodicity of fringes on the film. Although there are many techniques of exposing the interference patterns to form the Bragg grating 108, one embodiment may use a classical Lloyd's mirror interferometer. The interference fringes of constant spatial frequency are formed when a monochromatic, plane wave front is spatially divided in half by plane mirror and the two halves are superimposed later when the two are converged on the photosensitive polymer. The spatial frequency ν (fringes/mm) only depends on wavelength, λ, and the angle, φ, at which the two wave fronts interfere, which is expressed as $\nu = 2 \sin\phi/\lambda$.

For some embodiments, the Bragg grating 1302 may be made from electro-optic material such that the wavelength of light reflected by the Bragg grating 1302 changes in response to an applied voltage. That is, the deflection of light in the vertical direction using the Bragg grating 108 is based on the principle of electro-optically induced grating coupling of guided optical modes to substrate modes. An applied modulated signal on an electrode creates a periodic index-modulated Bragg grating in the propagation direction of the guided optical wave. The propagating modes interact with the index-modulated Bragg grating and are coupled phase matching radiating mode of the substrate. Thus the exit angle out of the waveguide core 210 becomes a function of optical index change.

For the vertical beam deflection, the Bragg grating 108 perturbs the waveguide modes in the region underneath the Bragg grating 108, thus causing each one of them to have a set of a spatial harmonics. The Bragg grating 108 scatters the incoming energy into space-harmonic fields that vary as $\exp[i(k_{xn}x - \omega t)]$ where $k_{xn}$ is related to grating period d by:

$$kxn = \beta_v + j\alpha = \beta_o + 2\pi\nu/d + j\alpha, \text{ where } \nu \text{ is } 0, \pm 1, \pm 2,$$

Unless permittivity of the Bragg grating 108 is much larger than the permittivity of the film, the fundamental term $\beta_o$ is closely equal to $\beta_{sw} = (2\pi n/\lambda) > k_o = 2\pi/\lambda$ of the propagating surface wave since the α factor is usually small, where β is the propagation constant of the particular mode (i.e., $\beta_v$ is the propagation constant of the ν mode). The α factor is due to the leakage of the energy into the diffracted orders scattered by the grating. Because of this the leakage, each scattered field is in the form of a leaky-wave beam. These waves radiate into the air region at an angles $$\Phi_v = \sin^{-1}(\beta_v/k_o), \text{ where } \nu \text{ is } 0, \pm 1, \pm 2,$$

M. D. Himel, X. Shi, X. Q. Hu, M. G. Moharam and K. H. Guenther, "Eletrooptic beam deflection using the leaky mode of a planar waveguide," IEEE Photonics Technol. Lett., Vol. 3, p. 921-923, 1991 and/or T. Tamir and S. T. Peng, "Analysis and Design of Grating Couplers," Applied Physics, Vol. 14, p. 235-254, 1977, are both incorporated herein by reference.

Since we are only interested in single outgoing beam into the upper air region 1308, the grating period, d, must be carefully selected such that $|\beta_v| > k_o$ for all $v \neq -1$. In the substrate region 212, there is a corresponding beam that exits into the substrate region 212, but the following condition $|\beta_{-1} > k_o n_s|$ (where $n_s$ is index of refraction of the substrate) must be also satisfied to reduce unnecessary loss due to unwanted high-order surface wave modes traveling in the substrate region 212.

Alternatively, based on the given electro-optical properties and geometry of the Bragg grating 108, the exit angle form the Bragg grating 108 may be calculated based on the following equations:

$$K_{zv} = \beta_v + j\alpha = \beta_o + \frac{2\pi\nu}{d} + j\alpha$$

$$k_o = \frac{2\pi n_{cladding}}{\lambda}$$

$$\beta_o = \frac{2\pi n_w}{\lambda}$$

$$\phi_v = \sin^{-1}\left(\frac{\beta_v}{k_o}\right)$$

$$= \sin^{-1}\left(\frac{\beta_o + \frac{2\pi\nu}{d}}{k_o}\right)$$

$$= \sin^{-1}\left(\frac{\frac{2\pi n_w}{\lambda} + \frac{2\pi\nu}{d}}{\frac{2\pi n_{cladding}}{\lambda}}\right)$$

$$= \sin^{-1}\left(\frac{n_w d + \nu\lambda}{n_{cladding} d}\right)$$

From the last equation shown above, by changing the index of refraction of the waveguide core 210 of the light beam 1306 radiating into the air region 1308 changes. The bending angle dependence of the period d of the Bragg grating 108 and refractive indices of electro-optic polymer is shown below. The maximum bending angle is approximately 6.077° when the index of electro-optic polymer changes from approximately 1.608 to approximately 1.615 and the Bragg grating 108 period d may be around 2055 nm.

With the active Bragg grating coupler 104, the vertical diffracting angle will vary with the change in the index by the input voltage. The existing angle and the range are carefully controlled by the grating period and the index of refraction of the electro-optic material.

Figure 14:
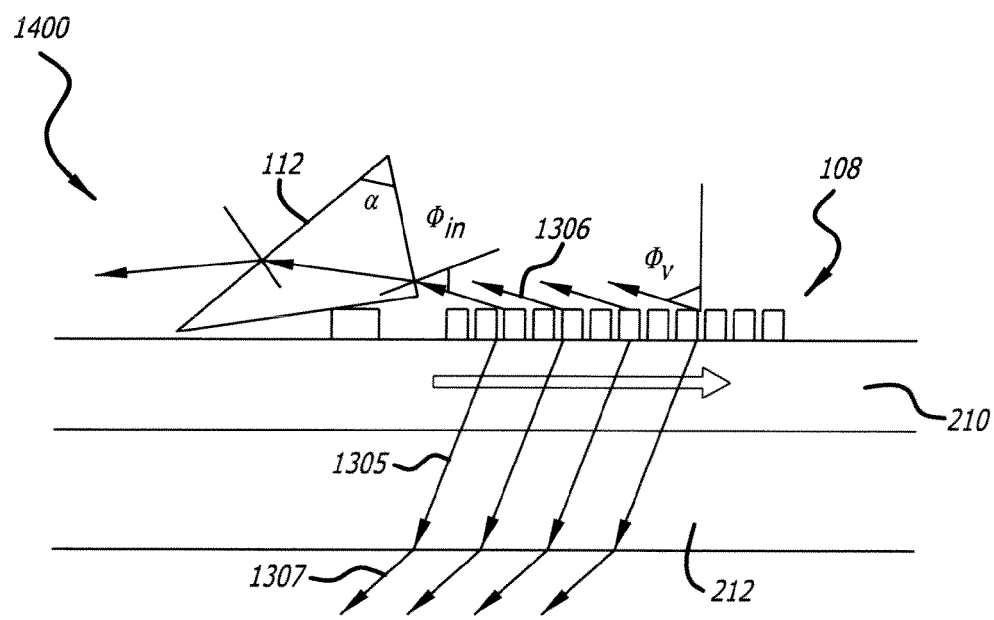
FIG. 14 illustrates a Bragg grating with an additional packaging prism according to an embodiment of the present invention.

For some embodiments, the prism 112 made from an electro-optic material, for example, may be placed in an opening in the packaging proximate to the Bragg grating 108 to further bend the light beam 1306 reflected from the Bragg grating 108 in the vertical direction. FIG. 14 illustrates the Bragg grating 108 with the additional prism 112 on top according to an embodiment of the present invention. For some embodiments, angle of interest a for the prism 112 may be fifty-three degrees and the angle of incidence bin into the prism 112 from the Bragg grating 108 may be twenty-three degrees. In this embodiment, the exit angle out of the Bragg grating 108 Φv may increase from approximately 6.077 degrees bending to approximately 22.1 degrees.

Figure 15:
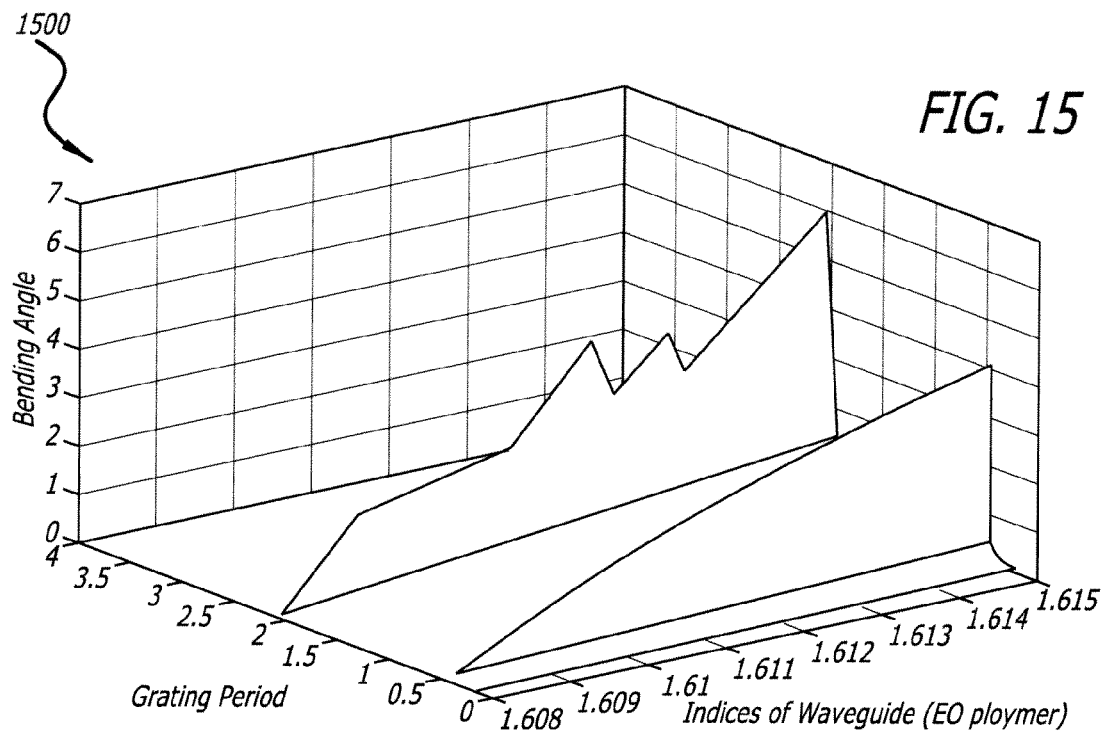
FIG. 15 is a three dimensional plot illustrating bending angle versus Bragg grating period versus indices of refraction of an electro-optic polymer used according to an embodiment of the present invention.
Figure 16:
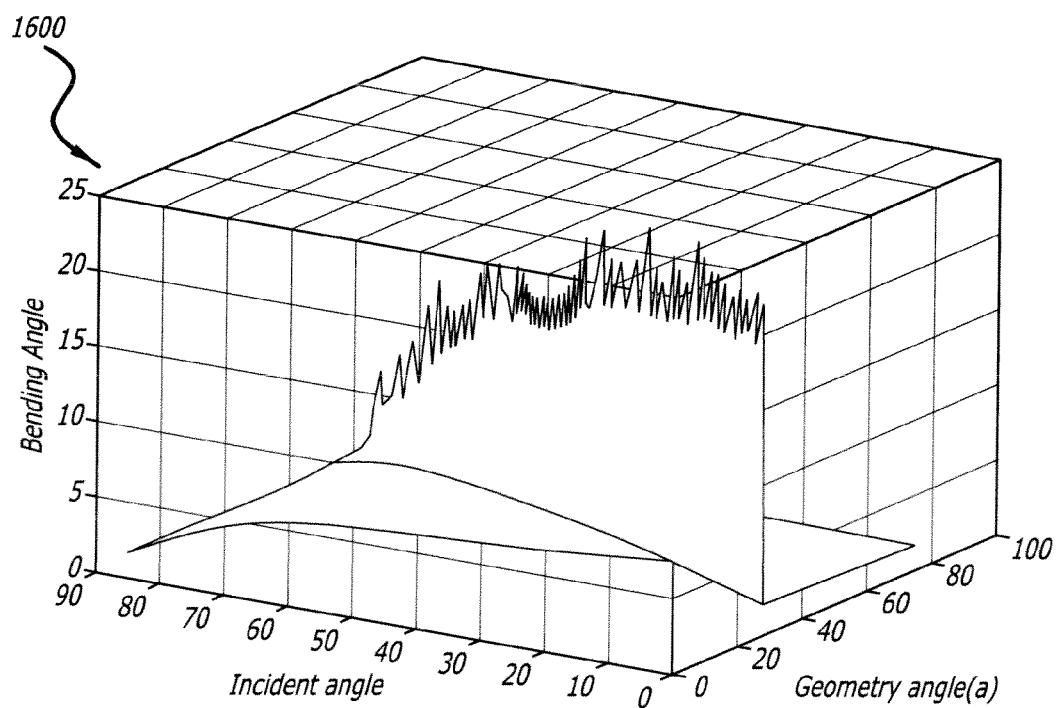
FIG. 16 is a three dimensional plot illustrating bending angle of a packaging prism versus angle of incidence at the prism versus angle of interest of the prism according to an embodiment of the present invention.

FIG. 15 is a three dimensional plot 1500 illustrating bending angle versus Bragg grating 108 period d versus indices of refraction of the electro-optic polymer used according to an embodiment of the present invention. FIG. 16 is a three dimensional plot 1600 illustrating bending angle of the prism 112 versus angle of incidence Φin at the prism 112 versus angle of interest a of the prism 112 according to an embodiment of the present invention.

For some embodiments, the lens 110 may be a spherical lens that is part of the packaging to further bend the light beam reflected from the Bragg grating 108. There may be an opening in the packaging for disposing the lens 110 proximate to the Bragg grating 108. The lens 110 may be positioned between the Bragg grating 108 and the photodetector array 114, such as after the prism 112. The lens 110 also may be used instead of the prism 112.

For some embodiments, the photodetector array 114 may be constructed from a silicon substrate. The material may also be the substrate used in the waveguide 118 and beam deflectors e.g., horizontal beam deflectors 106 and vertical beam deflectors 108). The silicon photodiode is known for light wave detection in the wavelength ranges of 0.4 to 1 µm due to its high responsibility around that wavelength spectrum. It has the virtues of high quantum efficiency, good linearity of response, large bandwidth, simple bias option and relatively easy to fabricate. Since pairs of red, green and blue photodetectors are required for capturing color images, these silicon based photodiodes offer the sufficient bandwidth in the visible spectrum (photodetector bandwidths must exceed 12.5 MHz for VGA and 19.8 MHz for SVGA video standard).

There are several methods for integrating the photodetector array 114 on a silicon substrate. In one embodiment, the photodetector array 114 includes one or more depletion layer photodiodes. The depletion-layer photodiode is essentially a reverse-biased semiconductor diode where reverse current is modulated by the electron-hole pairs produced in or near the depletion layer by the absorption of photons of light. The simplest depletion layer photodiode is a p-n junction diode. The diode is formed by boron diffusion (p-type silicon) to an n-type silicon substrate. A thick layer (several micrometers thick) of waveguide material made of either SiO₂ or silicon nitride is grown and used as a diffusion mask and later left as the waveguide. Metal electrodes may then be added to complete the structure.

To obtain a high current gain and maintain a high operating frequency, an avalanche photodetector (APD) structure may be implemented. In this device, a basic p-n structure is operated under a very high reverse bias. Setting precisely at the point of avalanche breakdown, carrier multiplication due to impact ionization results in significant gain in terms of increase in the carrier to photon ratio. The current multiplication for an avalanche diode can be as high as 4 orders in magnitude (based on commercially available photovoltaic photodiode and APD from UDT Sensor LTD).

Figure 17:
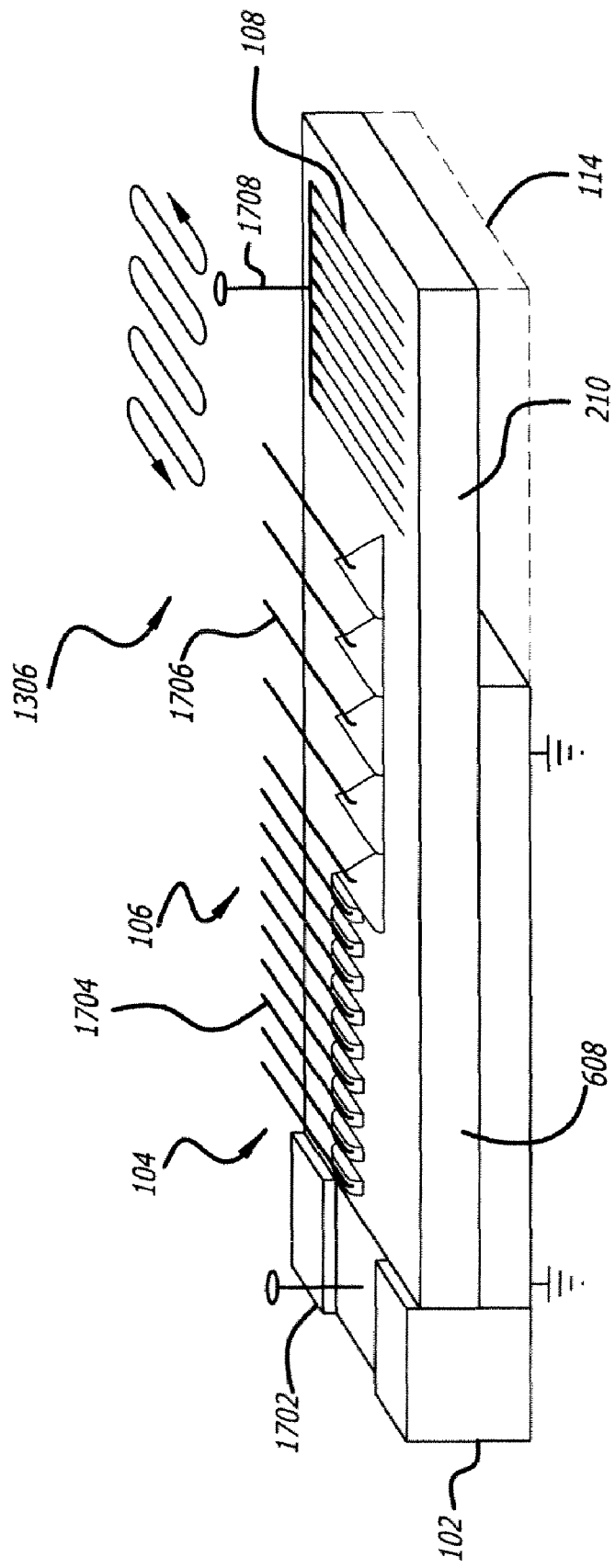
FIG. 17 illustrates a scanner according to an alternative embodiment of the present invention.

FIG. 17 illustrates a scanner 1700 according to an alternative embodiment of the present invention. In the illustrated embodiment, the scanner 1700 includes the light source 102 coupled to the lens array 104. The lens array 104, the prism array 106, and the Bragg grating 108 are disposed in or on the waveguide core 210. The photodetector array 114 is integrated in the scanner 1700. Light from the light source 102 is coupled to lens array 104, which focuses and collimates the light beam and couples the light beam to the prism array 106. The prism array 106 may deflect the light beam in a horizontal direction. The Bragg grating 108 may deflect the light beam in a vertical direction. The photodetector array 114 may detect the horizontally and vertically deflected light beam 1306 in its raster pattern. Power may be applied to the light source 102, lens array 104, the prism array 106, and the Bragg grating 108 via electrodes 1702, 1704, 1706, and 1708 respectively.

Figure 18:
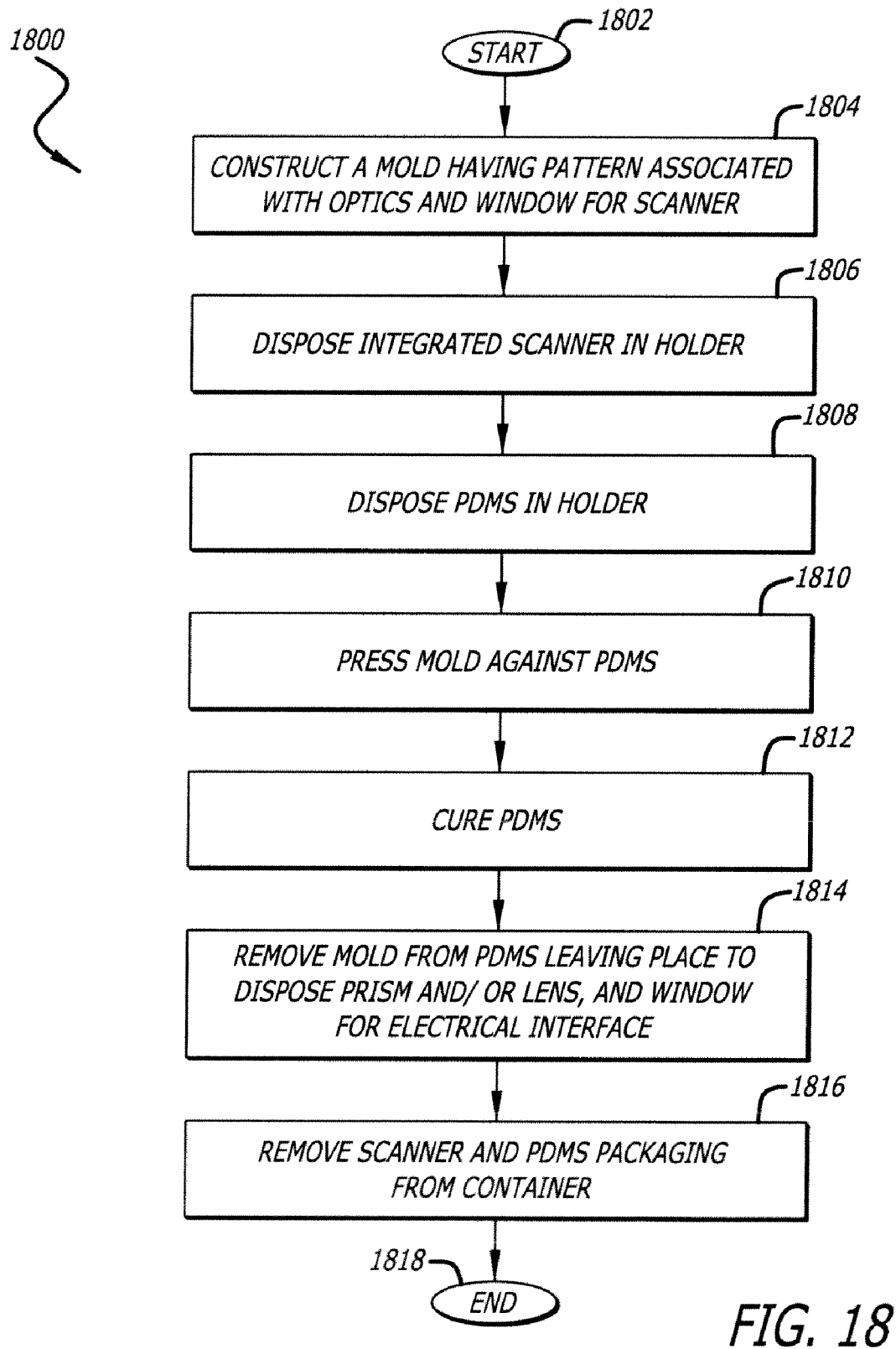
FIG. 18 is a flowchart illustrating a method for packaging a scanner according to an embodiment of the present invention.
Figure 19:
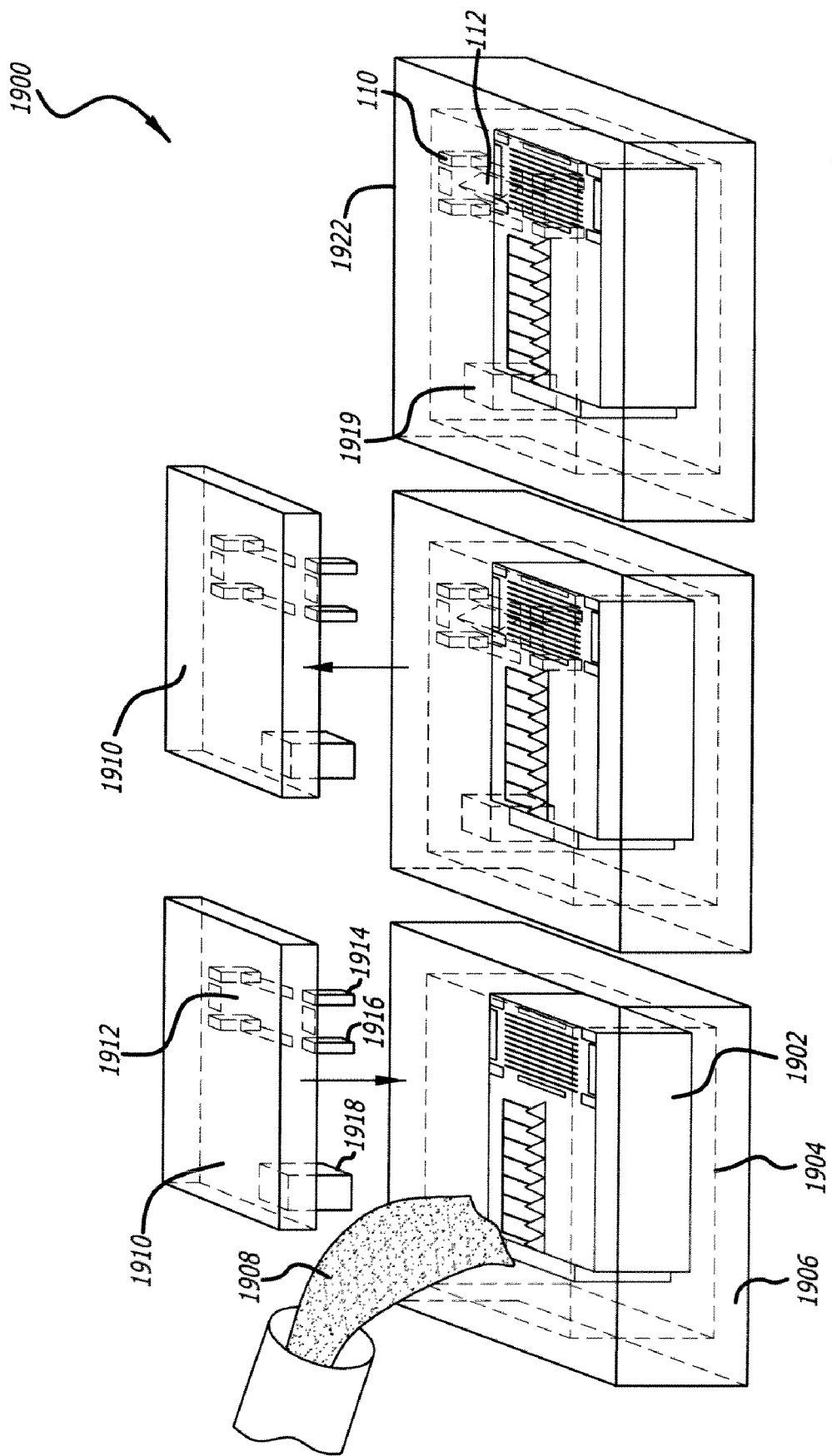
FIG. 19 is a diagram illustrating an approach to fabricating packaging for an integrated scanner according to an embodiment of the present invention.

FIG. 18 is a flowchart illustrating a method 1800 for packaging a scanner according to an embodiment of the present invention. For some embodiments, the packaging shields the scanner while leaving one surface of the scanner open for placement of a FIG. 18 is described with reference to FIG. 19, which is a diagram illustrating an approach to packaging an integrated scanner 1902 according to an embodiment of the present invention. The packaging may include a hole to accommodate the wires for coupling electrical signals to the scanner, an impression for the one or more lenses 110, and/or an impression for the prism 112.

Operation of the method 1800 begins with block 1802 in which control immediately passes to block 1804. In block 1804, a mold 1910 may be constructed. The mold 1910 may include a pattern having features 1912 for the prism 112, features 1916 and 1914 for the refractive lenses 110 for the photodetector array 114, and features 1919 for electrical interconnects for the input/output leads to the integrated scanner 1902. The mold 1910 may be made out of SU-8 photoresist (MicroChem Corporation XP SU-8 2000 series, Newton, Mass.) on a silicon wafer where large aspect ratio of microstructure can be faithfully reproduced. The patterns may be formed on the SU-8 photoresist by exposing the SU-8 photoresist with the desired patterns using typical photolithography.

In block 1806, the integrated scanner 1902 is disposed in a holder 1904. Ror some embodiments, the integrated scanner 1902 may be placed inside an aluminum container where the holder 1904 is machined to a depth matching the packaging thickness.

In block 1808, packaging material 1908 is disposed in the holder 1904. For some embodiments, a polydimethylsiloxane (PDMS) polymer solution may be poured into the holder 1904 and the holder 1904 filled. Other packaging materials also are suitable. For example, the packaging material 1908 may be any suitable biocompatible or non-biocompatible material. Other suitable materials include polyurethane, latex, or the like.

In block 1810, the mold 1910 having the patterns for the wires, prism and lens may be pressed against the packaging material 1908.

In block 1812, the packaging material 1908 may be cured.

In block 1814, the mold 1910 may be removed from the packaging material 1908 and the holder 1904. For some embodiments, the cured packaging 1908 includes a hole at 1919 to accommodate the wires for coupling electrical signals to the scanner, one or more lenses 110, and/or the prism 112.

In block 1816, the scanner 1902 and packaging 1908 may be removed from the holder 1904.

In block 1818, the method 1800 ends.

Figure 20:
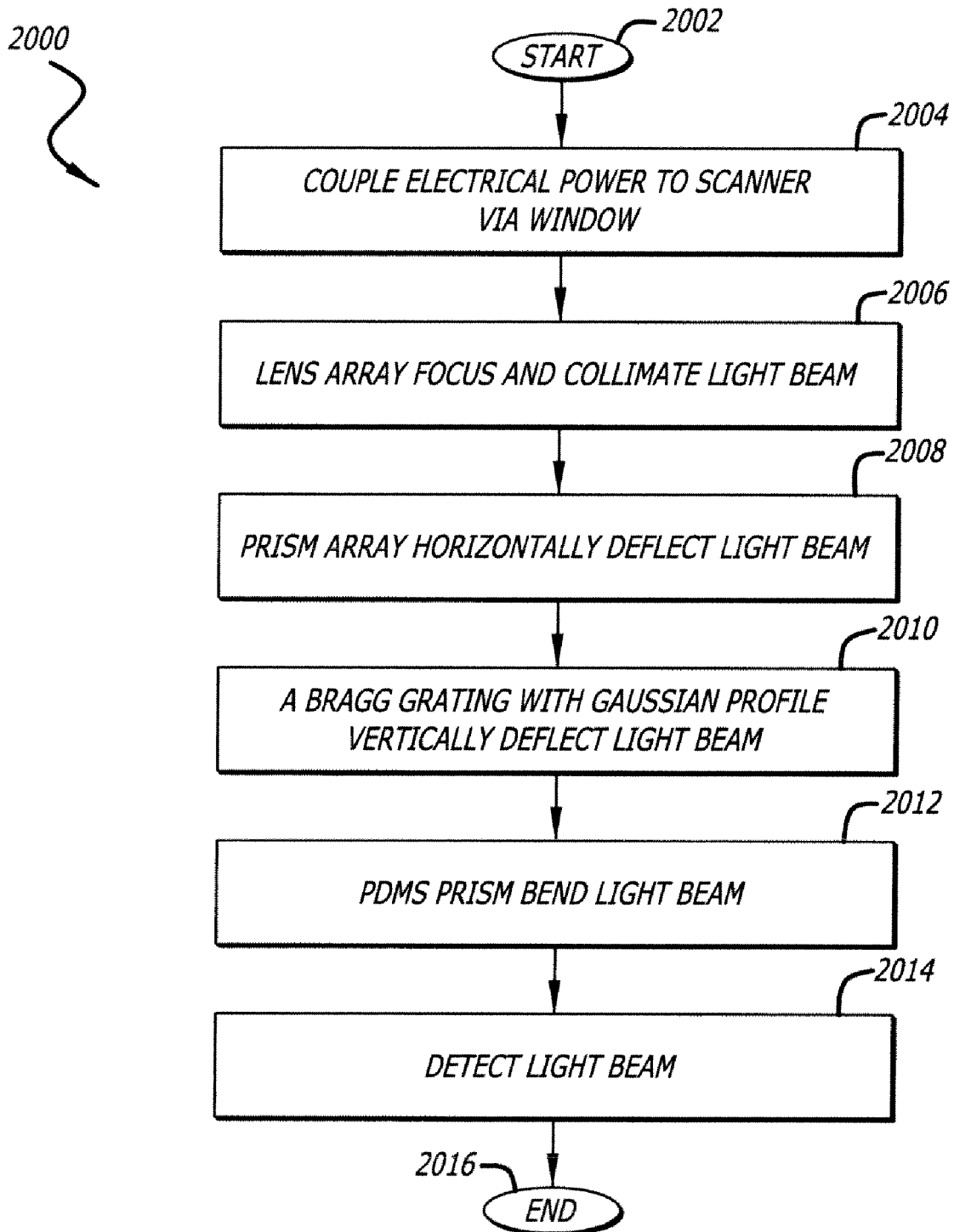
FIG. 20 is a flowchart illustrating a method 2000 for operating a scanner according to an embodiment of the present invention.

FIG. 20 is a flowchart illustrating a method 2000 for operating a scanner according to an embodiment of the present invention. The method 2000 begins with block 2002 and control passes to block 2004.

In block 2004, electrical power is coupled to an integrated scanner via an opening in PDMS packaging material. For some embodiments, an applied voltage may be used to control the refractive index of electro-optic materials in the scanner and/or to power a light source or other electrically operated devices in the scanner.

In block 2006, the light source generates a light beam, which is coupled to a lens array. The lens array may focus and collimate the light beam using a series of convex and concave lenses. Alternatively, the lens array may focus and collimate the light beam using a series of lenses whose geometry may be the same but which may be made of electro-optic material. The lens array may change the amount focus and collimation based on an applied voltage.

In block 2008, a prism array having several prisms of varying geometries deflects the collimated and focused light beam in a horizontal direction. The prisms may be made from electro-optic material and if a voltage is applied to the prisms the index of refraction may change such that the amount and direction of deflection may change.

In block 2010, a Bragg grating having Gaussian profile deflects the horizontally deflected light beam in a vertical direction. The Bragg grating may be made from electro-optic material and if a voltage is applied to the Bragg grating the index of refraction may change such that the amount and direction of deflection may change.

In block 2012, a prism fabricated in the PDMS packaging further deflects the vertically deflected light beam towards a photodetector array. Alternatively or in addition to, one or more lenses fabricated in the PDMS packaging further bends the vertically deflected light beam towards a photodetector array. If a voltage is applied to the PDMS packaging the index of refraction may change such that the amount and direction of bending imparted by the prism and/or lenses may change.

In block 2014, the photodetector array detects the horizontally and vertically deflected light in a raster pattern.

In block 2014, the method 2000 ends.

Potential applications of display systems implemented according to embodiments of the present invention may vary from the military, health, manufacturing, security, to a computer monitor and a high definition television.

As described above, embodiments of the present invention may be implemented using hardware, software, or a combination thereof. In implementations using software, the software may be stored on a machine-accessible medium. A machine-accessible medium includes any mechanism that may be adapted to store and/or transmit information in a form accessible by a machine (e.g., a computer, network device, personal digital assistant, manufacturing tool, any device with a set of one or more processors, etc. For example, a machine-accessible medium includes recordable and non-recordable media (e.g., read only memory (ROM, random access memory (RAM, magnetic disk storage media, optical storage media, flash memory devices, etc., as recess as electrical, optical, acoustic, or other form of propagated signals (e.g., carrier waves, infrared signals, digital signals, etc.

In the above description, numerous specific details, such as, for example, particular processes, materials, devices, and so forth, are presented to provide a thorough understanding of embodiments of the invention. One skilled in the relevant art will recognize, however, that the embodiments of the present invention may be practiced without one or more of the specific details, or with other methods, components, etc. In other instances, structures or operations are not shown or described in detail to avoid obscuring the understanding of this description.

Reference throughout this specification to "one embodiment" or "an embodiment" means that a particular feature, structure, process, block, or characteristic described in connection with an embodiment is included in at least one embodiment of the present invention. Thus, the appearance of the phrases "in one embodiment" or "in an embodiment" in various places throughout this specification does not necessarily mean that the phrases all refer to the same embodiment. The particular features, structures, or characteristics may be combined in any suitable manner in one or more embodiments.

The terms used in the following claims should not be construed to limit embodiments of the invention to the specific embodiments disclosed in the specification and the claims. Rather, the scope of embodiments of the invention is to be determined entirely by the following claims, which are to be construed in accordance with established doctrines of claim interpretation.

What is claimed is:

1. A scanner, comprising:
an optical device to receive an incident light beam at an angle of incidence, the optical device having disposed therein:
  a first refractive-based deflector to deflect the incident light beam towards a first direction, the first direction being in a horizontal direction, the first deflector comprising,
    a first prism having a first geometry,
    at least a second prism cascaded with the first prism, the at least a second prism having at least a second geometry different from the first geometry, wherein the light beam is to propagate in the first direction of the first and the at least a second prisms,
  a second deflector comprising a grating, the second deflector to deflect the first deflected light beam from the prisms towards a second direction perpendicular to the first direction, and
  a lens array disposed in or on the optical device to direct the incident light beam towards the first prism;
a light source to emit the incident light beam;
an optical fiber to couple incident light to the optical device, wherein the lens array comprises:
  at least one convex lens disposed in or on the optical device, the convex lens to focus the incident light;
  at least one concave lens disposed in or on the optical device, the concave lens to collimate the focused light beam, wherein the at least one convex lens is disposed between the first prism and the optical fiber, wherein the at least one concave lens is disposed between the at least one convex lens and the first prism, wherein the at least one convex lens is separated from the optical fiber by free space, and wherein the at least one concave lens is separated from the at least one convex lens by free space,
  a second convex lens disposed in or on the optical device, and
  a third convex lens disposed in or on the optical device, wherein the second convex lens is disposed between the at least one concave lens and the third convex lens, wherein the third convex lens is disposed between the second convex lens and the first prism, wherein the second convex lens is separated from the at least one concave lens by free space, wherein the third convex lens is separated from the second convex lens by free space, wherein the third convex lens is separated from the first prism by free space, wherein the first prism is separated from the at least a second prism by free space.

2. The scanner of claim 1, wherein the light source comprises a laser diode.

3. The scanner of claim 2, wherein the lens away comprises a layer of electro-optic material disposed in or on the optical device after the laser diode.

4. The scanner of claim 3, wherein the layer of electro-optic material comprises a first plano-convex lens.

5. The scanner of claim 4, further comprising at least a second layer of electro-optic material comprising at least a second plano-convex lens, wherein at least a second plano-convex lens is separated from the first plano-convex lens by free space.

6. The scanner of claim 1, wherein optical device includes a core comprising electro-optic material.

7. The scanner of claim 1, wherein the first prism is to disperse the incident light beam at a first angle, and wherein the second prism is to disperse the light from the first angle at a second angle different from the first angle.

8. The scanner of claim 1, wherein a difference between the angle of incidence and an angle of exit from the second deflector is determined by geometry of the first and second prisms, an input refractive index and an output refractive index of the first prism, and an input refractive index and an output refractive index of the second prism.

9. The scanner of claim 8, wherein the first and/or second prisms comprise electro-optic material, wherein the electro-optic material is to change refractive indexes in response to a voltage being applied, and wherein a difference between the angle of incidence and an angle of exit from the second deflector is further determined by the change in refractive indexes of the first and/or second prisms.

10. The scanner of claim 8, wherein the first and/or second prisms comprise liquid crystal material, wherein the liquid crystal material is to change refractive indexes in response to a voltage being applied, and wherein the a difference between the angle of incidence and an angle of exit from the second deflector is further determined by the change in refractive indexes of the first and/or second prisms.

11. The scanner of claim 1, wherein the grating comprises a Bragg grating formed from an electro-optic material selected from among as liquid crystal material, a III-V material, and an electro-optic polymer.

12. The scanner of claim 11, wherein the Bragg grating includes a groove-depth modulated non-uniform shape and a substantially Gaussian profile.

13. The scanner of claim 12, further comprising:
means for receiving electrical power; and
an integrated detector array coupled to detect the reflected light.

14. A scanner, comprising:
an optical device to receive an incident light beam at an angle of incidence, the optical device having disposed therein:
a first refractive-based deflector to deflect the incident light beam towards a first direction, the first direction being in a horizontal direction, the first deflector comprising:
a first prism having a first geometry,
at least a second prism cascaded with the first prism, the at least a second prism having at least a second geometry different from the first geometry, wherein the light beam is to propagate in the first direction of the first and the at least a second prisms,
a second deflector comprising a grating, the second deflector to deflect the first deflected light beam from the prisms towards a second direction perpendicular to the first direction, and
a lens array disposed in or on the optical device to direct the incident light beam towards the first prism;
a light source to emit the incident light beam;
an optical fiber to couple incident light to the optical device, wherein the lens away comprises:
at least one convex lens disposed in or on the optical device, the convex lens to focus the incident light,
at least one concave lens disposed in or on the optical device, the concave lens to collimate the focused light beam, wherein the at least one convex lens is disposed between the first prism and the optical fiber, wherein the at least one concave lens is disposed between the at least one convex lens and the first prism, wherein the at least one convex lens is separated from the optical fiber by free space, and wherein the at least one concave lens is separated from the at least one convex lens by free space,
a second convex lens disposed in or on the optical device, and
a third convex lens disposed in or on the optical device, wherein the second convex lens is disposed between the at least one concave lens and the third convex lens, wherein the third convex lens is disposed between the second convex lens and the first prism, wherein the second convex lens is separated from the at least one concave lens by free space, wherein the third convex lens is separated from the second convex lens by free space, wherein the third convex lens is separated from the first prism by free space, wherein the first prism is separated from the at least a second prism by free space;
wherein at least one of the first, second, and/or third convex lenses has geometry that is different from geometry of remaining convex lenses.

15. A method for packaging a scanner, the method comprising:
disposing the scanner in a container, the scanner having a first prism disposed in or on an optical device and operationally coupled to a second prism disposed in or on the optical device, the scanner having further a Bragg grating disposed in or on the optical device, the Bragg grating operationally coupled to the second prism;
disposing a biocompatible material in the container; and
impressing a pattern into the biocompatible material, wherein impressing the pattern into the biocompatible material comprises making a depression, the depression shaped to receive a spherical lens.

16. The method of claim 15, further comprising impressing a second pattern into the biocompatible material, wherein impressing the second pattern into the biocompatible material comprises making an opening for the scanner to receive electrical power.

17. The method of claim 15, further comprising impressing a second pattern into the biocompatible material, wherein impressing the second pattern into the biocompatible material comprises making a depression, the depression shaped to receive a prism.

* * * * *

UNITED STATES PATENT AND TRADEMARK OFFICE
CERTIFICATE OF CORRECTION

PATENT NO. : 7,700,908 B2
APPLICATION NO. : 11/760622
DATED : April 20, 2010
INVENTOR(S) : Wang et al.

It is certified that error appears in the above-identified patent and that said Letters Patent is hereby corrected as shown below:

In Column 1, line 5, delete "SPONSERED" and replace with -- SPONSORED --.

In Column 17, line 59, delete "±2," and replace with -- ±2,... --.

In Column 18, line 4, delete "±2," and replace with -- ±2,... --.

Column 22, lines 24 and 25 (Claim 1, lines 7 and 8), delete "comprising," and replace with -- comprising: --.

Column 23, line 3 (Claim 3, line 1), delete "away" and replace with -- array --.

Column 24, line 10 (Claim 14, line 24), delete "away" and replace with -- array --.

Signed and Sealed this

Nineteenth Day of October, 2010

David J. Kappos
*Director of the United States Patent and Trademark Office*